US006829501B2

(12) United States Patent
Nielsen et al.

(10) Patent No.: US 6,829,501 B2
(45) Date of Patent: Dec. 7, 2004

(54) PATIENT MONITOR AND METHOD WITH NON-INVASIVE CARDIAC OUTPUT MONITORING

(75) Inventors: Eric Nielsen, Milwaukee, WI (US); Patrick A. Van Ryzin, Pewaukee, WI (US)

(73) Assignee: GE Medical Systems Information Technologies, Inc., Milwaukee, WI (US)

(*) Notice: Subject to any disclaimer, the term of this patent is extended or adjusted under 35 U.S.C. 154(b) by 158 days.

(21) Appl. No.: 10/034,351

(22) Filed: Dec. 20, 2001

(65) Prior Publication Data

US 2003/0120164 A1 Jun. 26, 2003

(51) Int. Cl.[7] .................................................. A61B 5/04
(52) U.S. Cl. ........................................................ 600/513
(58) Field of Search ................................. 600/500–528

(56) References Cited

U.S. PATENT DOCUMENTS

| | | | |
|---|---|---|---|
| 5,309,917 A | * | 5/1994 | Wang et al. |
| 5,319,363 A | * | 6/1994 | Welch et al. .......... 340/825.36 |
| 5,456,261 A | | 10/1995 | Luczyk |
| 5,956,013 A | * | 9/1999 | Raj et al. ..................... 345/208 |
| 6,221,012 B1 | * | 4/2001 | Maschke et al. |

OTHER PUBLICATIONS

Solar® 7000/8000 Patient Monitor Operator's Manual, Software version 6, 2000711–006, Revision A, Jan. 14, 2000, 305 pages, GE Marquette Medical Systems, Inc., Milwaukee, Wisconsin.

GE Medical Systems, Press Room, News Release dated Mar. 29, 2000 "CardioDynamics and GE Marquette Medical Systems Announce Largest Multi–System BioZ. Order to Nationally–Recognized Cardiovascular Center", http://www.gemedicalsystems.com/cgi–bin/print/print.cgi.

GE Medical Systems, Press Room, News Release dated Jul. 11, 2000 "GE Marquette Medical Systems and CardioDynamics Announce Joint Technology Development Agreement", http://www.gemedicalsystems.com/cgi–bin/print/print.cgi.

GE Medical Systems, Monitoring Systems, Non–invasive Hemodynamic Monitoring http://www.gemedicalsystems.com/monitor/products/modular/icg_m.

"GE Medical Systems Information Technologies and CardioDynamics Preview BioZ® ICG Module for Solar® Patient Monitoring Family at American Heart Association Meeting", Nov. 13, 2000 http://www.cardiodynamics.com/ir/press_releases/cd_pr111300.html.

(List continued on next page.)

*Primary Examiner*—Scott M. Getzow
(74) *Attorney, Agent, or Firm*—Andrus, Sceales, Starke & Sawall, LLP

(57) ABSTRACT

A patient monitoring system comprises a non-invasive cardiac output sensor and a patient monitor console. The non-invasive cardiac output sensor is capable of acquiring a signal from a patient indicative of blood flow through a heart of the patient. The patient monitor console includes an analysis module and a display. The analysis module is coupled to the non-invasive cardiac output sensor and processes the signal from the patient indicative of blood flow to produce a value pertaining to cardiac output. The display is coupled to the analysis module and displays the value pertaining to cardiac output.

19 Claims, 21 Drawing Sheets

OTHER PUBLICATIONS

GE Medical Systems, Press Room, News Release dated Jun. 20, 2001 "GE Introduces the World's First Non–Invasive Hemodynamic Patient Monitoring System with CardioDynamics' ICG Technology", http://www.gemedicalsystems.com/cgi–bin/print/print.cgi.

Solar® 7000/8000 Patient Monitor Operator's Manual, Software Version 7, 2000711–032 Revision A Chapters 1, 10, 14 and 19.

Dash® 3000/4000 Patient Monitor Operator's Manual, Software Version 2, 2000966–069 Revision A Chapters 1, 4, 6, 8, 10, 11, 12, 13, 14, 15, 16, 17, 18.

BioZ.com™ Operator/Service Manual, Mar. 2000.

"The View Within: The Emerging Technology of Thoracic Electric Bioimpedance"; Lasater M.; vol. 21, No. 3, pp. 97–101; Nov. 1998; Critical Care Nursing Quarterly.

"Advances in Noninvasive Hemodynamic Monitoring"; Clontz RL; Issue 167, pp. 47–50; Oct. 1997; Medical Electronics.

"Impedance Cardiography: Noninvasive Measurement of Cardiac Stroke Volume and Thoracic Fluid Content"; Strobeck JE; pp. 56–59; Mar./Apr. 2000; Congestive Heart Failure.

"Noninvasive Cardiac Output Measurement"; Bernstein DP; Chapter 18, pp. 159–185; In: "Textbook of Critical Care, Second Edition"; Philadelphia, WB Saunders Co. (1989).

"Electrophysiologic Principles and Theory of Stroke Volume Determination by Thoracic Electrical Bioimpedance"; Osypka, MJ, et al.; vol. 10, No. 3, pp. 385–399; Aug. 1999; AACN Clinical Issues.

* cited by examiner

PATIENT MONITOR AND METHOD WITH NON-INVASIVE CARDIAC OUTPUT MONITORING

FIELD OF THE INVENTION

The invention relates to a patient monitoring systems and methods and, particularly, to patient monitoring systems and methods for non-invasively monitoring cardiac output of a patient.

BACKGROUND OF THE INVENTION

There is an ongoing need for medical equipment and procedures that allow for quick and accurate diagnosis of patient conditions. For example, in the context of myocardial infarctions, patients frequently arrive at emergency rooms of hospitals complaining of chest pain. The chest pain may be a symptom indicating the patient is experiencing a myocardial infarction or, alternatively, the chest pain may be a symptom indicating the patient is experiencing a lesser medical condition such as heartburn or indigestion. Statistics show that quickly identifying whether a patient is having a myocardial infarction and treating such condition may minimize the amount of damage to the heart. Therefore, there is an ongoing need for systems that can be used to quickly identify whether a patient has had a myocardial infarction.

Additionally, in the context of congestive heart failure, patients benefit from the use of intermittent inotrope infusions, such as milrinone. These infusions, while usually beneficial, are also costly and carry attendant risks such as dysrhythmias and infection, from both indwelling infusion catheters and pulmonary artery catheters used to document the necessity of inotropic support. Therefore, there is an ongoing need for systems that can be used to conduct a pre-assessment of patients scheduled for intermittent inotrope infusion to ascertain whether or not such infusions are needed.

Further, in the context of circulatory deficiencies, acutely ill emergency room patients often have circulatory deficiencies that ultimately lead to shock, organ failure, and death. Early diagnosis is often difficult and subjective, and therefore these deficiencies are currently diagnosed in late stages when therapy is ineffective. Diagnosing these circulatory deficiencies in their early stages allows the patient to be treated before the course of these deficiencies becomes irreversible. Therefore, there is an ongoing need for systems that can be used to assist early detection of such circulatory deficiencies.

It has been found that cardiac output monitoring is useful for diagnosing medical conditions such as those described above. Impedance cardiography techniques for non-invasive monitoring cardiac output are known in the art. However, existing devices that are capable of monitoring cardiac output are cumbersome to utilize. Therefore, improved patient monitoring systems and methods that are capable of monitoring cardiac output would be highly beneficial.

BRIEF SUMMARY OF THE INVENTION

According to one preferred aspect, an embodiment of a patient monitoring system comprises a non-invasive cardiac output sensor, a multi-lead electrocardiogram (ECG) sensor, and a patient monitor console. The non-invasive cardiac output sensor being capable of acquiring a signal from a patient indicative of blood flow through a heart of the patient. The multi-lead ECG sensor comprises a plurality of ECG electrodes capable of acquiring a plurality of ECG signals from the patient. The patient monitor console includes an analysis module and a display. The analysis module is coupled to the non-invasive cardiac output sensor and to the multi-lead ECG sensor, and processes the signal from the patient indicative of blood flow to produce a value pertaining to cardiac output. The display is coupled to the analysis module, and displays the value pertaining to cardiac output and an ECG waveform generated based on the ECG signals.

According to another preferred aspect, an embodiment of a patient monitoring system comprises a non-invasive cardiac output sensor, a communication interface, and a patient monitor console. The non-invasive cardiac output sensor is capable of acquiring a signal from a patient indicative of blood flow through a heart of the patient. The communication interface is capable of establishing a communication link between the patient monitoring system and a local area network of a medical facility in which the patient monitoring system is located. The patient monitor console includes an analysis module and a display. The analysis module is coupled to the non-invasive cardiac output sensor, and processes the signal from the patient indicative of blood flow to produce a value pertaining to cardiac output. The display is coupled to the analysis module, and displays the value pertaining to cardiac output. The communication interface is capable of transmitting the value pertaining to cardiac output over the local area network.

Other features and advantages of the invention will become apparent to those skilled in the art upon review of the following detailed description, claims, and drawings.

DETAILED DESCRIPTION OF PREFERRED EMBODIMENTS

Figure 1:
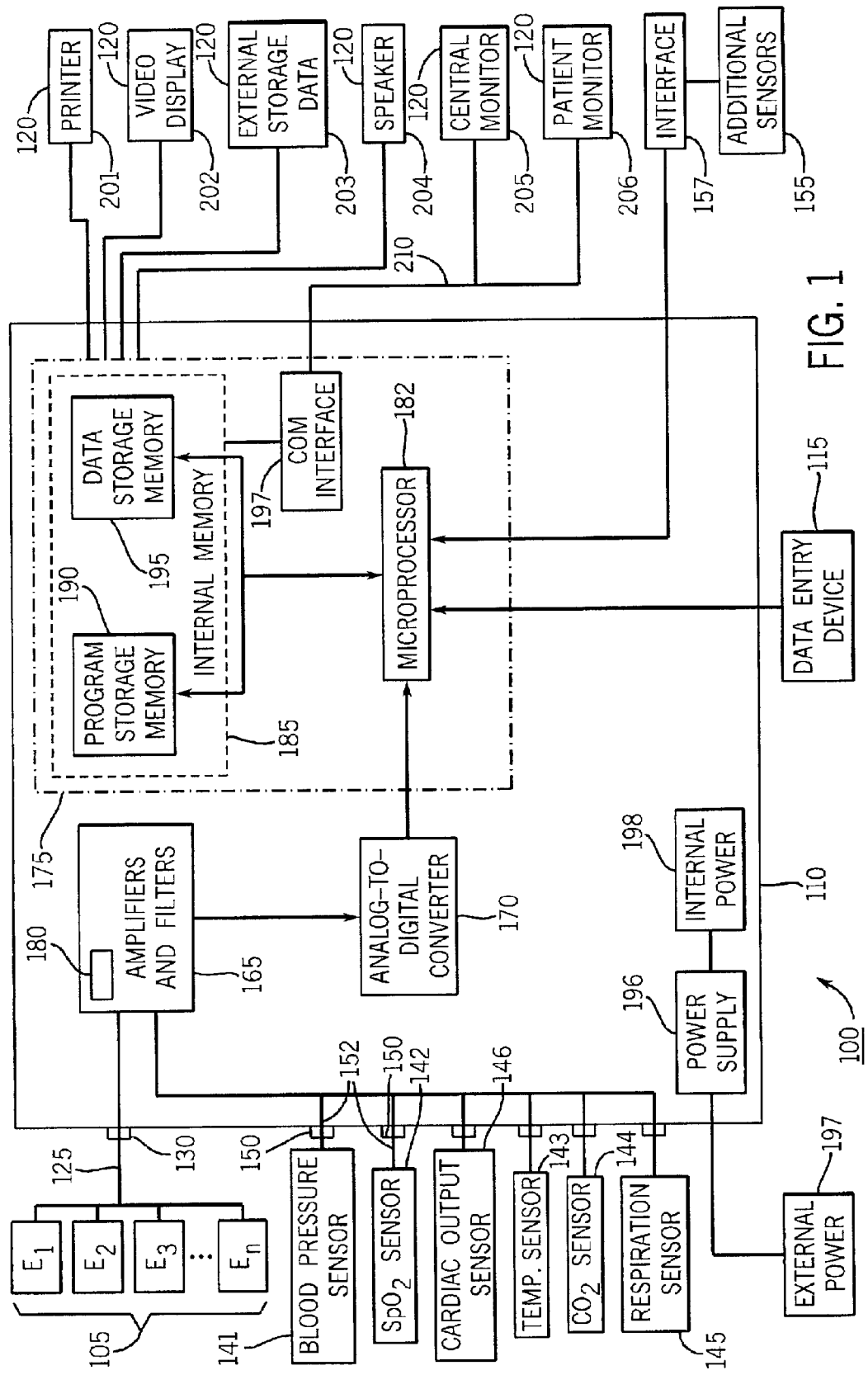
FIG. 1 is a schematic diagram of a patient monitoring system according to a preferred embodiment of the invention.

Referring now to FIG. 1, a patient monitoring system 100 according to a preferred embodiment of the invention is schematically shown. In general terms, the system 100 includes one or more input devices 105, a patient monitor console 110, a data entry device 115 connected to the console 110, and one or more output devices 120 connected to the console 110. In the preferred embodiment, the patient monitor console is portable and is implemented using a GE Medical Systems Information Technologies, Inc. DASH® 3000 Pro™ brand portable monitor, modified to incorporate additional features described below.

The input devices 105 include a multi-lead ECG sensor comprising a plurality of electrodes $E_1$, $E_2$ . . . $E_n$ that are connectable to a patient. The electrodes are capable of acquiring ECG signals generated by the patient. The number of electrodes $E_1$, $E_2$ . . . $E_n$ may vary. For example, three, five, ten or twelve ECG leads may be used. In the preferred embodiment, the number of electrodes is equal to ten and the leads are connected to the patient in a standard twelve-lead configuration for 12SL processing.

The electrodes $E_1$, $E_2$ . . . $E_n$ are connected to the console 110 by an interface cable 125. The interface cable 125 provides direct communication between the electrodes $E_1$, $E_2$ . . . $E_n$ and an input port 130. The input port 130 comprises a connector that mates with a corresponding connector on the cable 125. The interface cable 125 allows for transmission of the acquired ECG signals from the patient to the console 110. The interface cable 125 is preferably a passive cable but, alternatively, the cable 125 may contain active circuitry for amplifying and combining the ECG signals into ECG leads (discussed further below). In other embodiments, the electrodes $E_1$, $E_2$ . . . $E_n$ may be in communication with the console 110 through a telemetry-based transmitter transmitting a radio frequency ("RF") signal to one or more antennas connected to console 110 through a conventional RF receiver.

The input devices 105 further include one or more sensors which are connectable to the patient and acquire additional physiological signals from the patient. Example sensors may include an invasive and/or non-invasive blood pressure sensor 141, a pulse-oximetry sensor 142, a temperature sensor 143, a carbon dioxide sensor 144, a respiration sensor 145, and a cardiac output sensor 146. Similar to electrodes $E_1$, $E_2$ . . . $E_n$ and for the embodiment shown, the sensors 140 may be connected to the console 110 at respective input ports 150 by interface cables 152 or via telemetry transmitters as described above.

Additional sensors may also be connected to the console 110. For example, many commercially available sensors are capable of transmitting data via an RS-232 link. In FIG. 1, respective RS-232 links may be used to transmit data from a plurality of additional sensors 155 to an interface 157, with the interface 157 retransmitting the data to the console 110 by a serial or network link. The sensors 155 may be the same or different types of sensors as the sensors 141–146.

The input signals from the sensors 141–146 are processed at the console 110 by amplifying-and-filtering circuitry 165, analog-to-digital (A/D) conversion circuitry 170, and an analysis module 175. Depending on the manner in which the sensors 155 provide data to the console 110, the signals from the sensors 155 may be processed by some or all of this circuitry as well. The amplifying-and-filtering circuitry 165, the A/D conversion circuitry 170, and the analysis module 175 may be discrete circuitry, may be incorporated as an integrated circuit (e.g., an application specific integrated circuit), or may be a combination of both.

The amplifying-and-filtering circuitry 165 receives the physiological signals from the input ports 130 and 150, and amplifies and filters (i.e., conditions) the physiological signals. For example, the amplifying-and-filtering circuitry 165 includes an instrumentation amplifier 180. The instrumentation amplifier 180 receives the ECG signals, amplifies the signals, and filters the signals to create a multi-lead ECG. The number of leads of the multi-lead ECG may vary without changing the scope of the invention.

The A/D conversion circuitry 170 is electrically connected to the instrumentation amplifier 180. The A/D conversion circuitry 170 receives the amplified and filtered physiological signals and converts the signals into digital physiological signals (e.g., a digital multi-lead ECG). The digital physiological signals are then provided to the analysis module 175 which is electrically connected to the A/D conversion circuitry 170.

The analysis module 175 reads the digital physiological signals, analyzes the signals from the A/D conversion circuitry 170, and displays the signals and the resulting analysis to an operator. The analysis module 175 includes a controller or microprocessor 182 and internal memory 185. The internal memory 185 includes program storage memory 190 for storing a software program and data storage memory 195 for storing data. The microprocessor 182 executes the software program to control the monitoring system 100. The implementation of the software program, including the operator interface, is discussed in further below.

The console 110 also includes a power supply 196. The power supply 196 powers the console 110 and receives input power from either an external power source 194 or an internal power source 198. The console 110 is preferably capable of being connected to the external power source 194 by way of a port or docking station. The internal power source 160 is preferably a rechargeable battery and is capable of being recharged when the console 110 is received by the docking station.

The data-entry device 115 allows an operator (e.g., a technician, nurse, doctor, etc.) to enter data into the console 110. The data-entry device 115 may be incorporated within the console 110 (e.g., a dial control device) or, alternatively, may be a stand-alone device (e.g., a stand-alone keyboard). Other example data-entry devices 115 include a keypad, a touch screen, a pointing device (e.g., a mouse, a trackball), etc.

The output devices 120 preferably include a printer 201, a display 202, a storage device (e.g., a magnetic disc drive, a read/write CD-ROM, etc.) 203, and a speaker 204, any or all of which may be integrally provided with the console 110. The output devices 120 further include a central monitor 205 and one or more additional patient monitors 206. The patient monitoring system 100 is connected to the central monitor 205 and the patient monitor 206 by way of a communication interface 197 and a medical communication network 210 of the medical facility in which the patient monitoring system is located. Of course, other output devices may be added or attached (e.g., a defibrillator), and/or one or more output devices may be incorporated within the console 110. Additionally, not all of the input devices 105 and output devices 120 are required for operation of the monitoring system 100.

Figure 2:
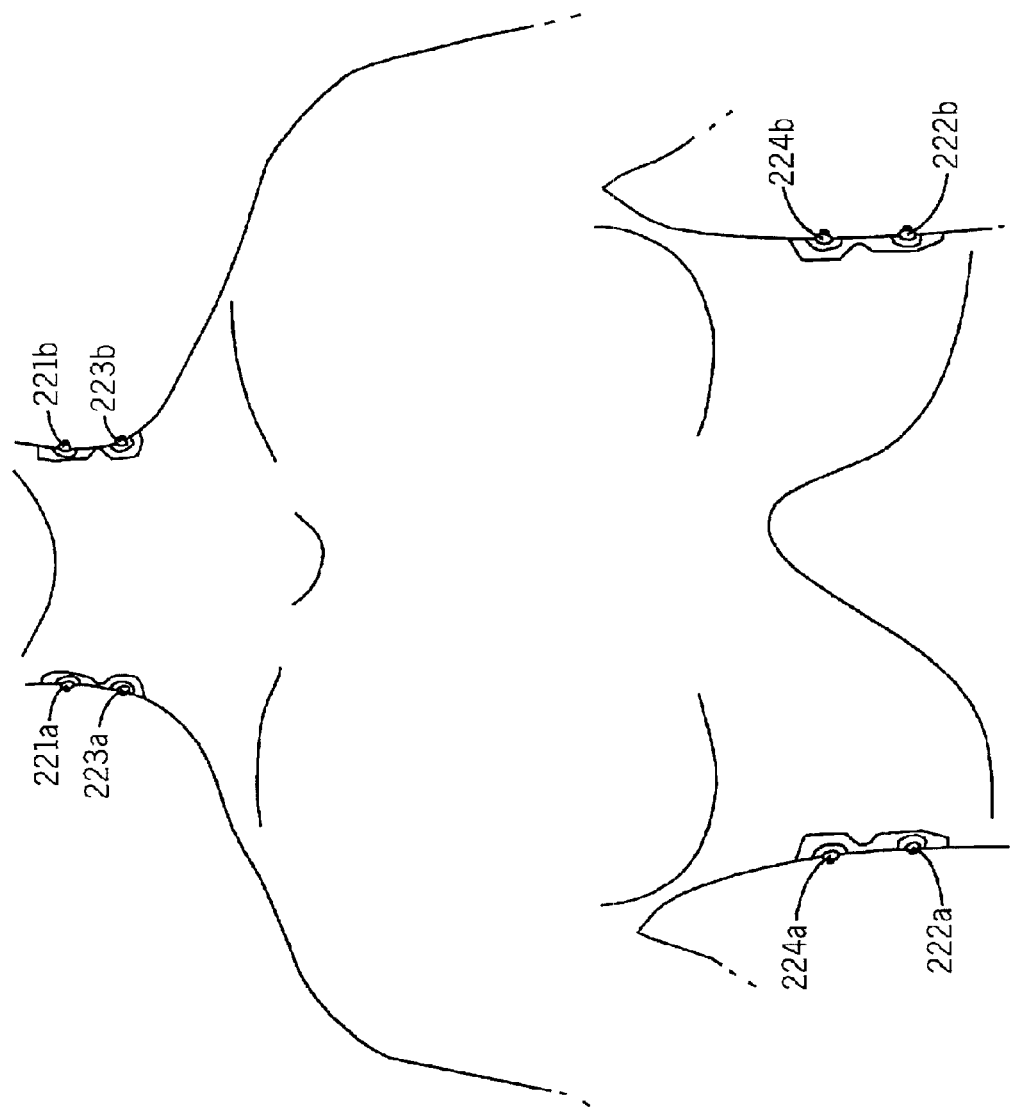
FIG. 2 is a diagram showing electrode placement for a preferred non-invasive cardiac output sensor used in the patient monitoring system of FIG. 1.

Referring now to FIG. 2, the cardiac output sensor 146 is shown in greater detail. The cardiac output sensor 146 is non-invasive and preferably employs impedance cardiography to measure cardiac output. Impedance cardiography utilizes changes in thoracic electrical impedance to estimate changes in blood volume in the aorta and fluid volume in the thorax. The changes in thoracic electrical impedance are measured by measuring changes in voltage in response to an applied current. Specifically, an excitation signal is applied to the patient using electrodes 221a–221b and 222a–222b The electrodes 221a14 221b are placed vertically along each side of the neck, directly below the earlobe. The superior thoracic electrodes 222a–222b are located in-line with the xiphoid process on either side of the thorax along the mid-auxiliary line. The electrodes 221a–221b are positioned directly opposite each other, as are the electrodes 222a–222b. The excitation signal is a low amplitude (e.g., 1–4 milliamps), high frequency (e.g., 30–100 kHz), constant magnitude alternating current which is applied to the thoracic volume.

A response signal indicative of blood flow is produced in response to the excitation signal. The response signal is acquired by another pair of electrodes 223a–223b below the current injecting electrodes 221a–221b on the neck, and another pair of electrodes 224a–224b above the current injecting electrodes 222a–222b on the lower thorax. When the constant magnitude current is applied to the thorax, the voltage of the response signal is proportional to the impedance between the electrodes 223a–223b and the electrodes 224a–224b. This impedance is a function of an amount of blood located in a blood flow path that passes through the heart of the patient.

Thus, in the embodiment of FIG. 2, the total thoracic impedance Z(t) at any time is equal to the overall thoracic impedance $Z_0$ plus changes in impedance ΔZ corresponding to both the ventilation and pulsatile blood flow: $Z(t)=Z_0+\Delta Z(t)$. The overall thoracic impedance $Z_0$ is determined by the impedances of the various tissues of the thorax including cardiac and skeletal muscle, fat, lung, bone, vascular tissue, and the ratio of air to liquids in the thorax. The changes in impedance ΔZ corresponding to both the ventilation and pulsatile blood flow result from the fact that blood is highly conductive. Thus, blood volume increases in the thoracic aorta and, to a lesser extent, in the pulmonary artery, are presumed to cause a decrease in impedance to current flow. Beat-to-beat dynamic impedance (ΔZ(t)), for practical purposes, is the impedance change due to ventricular ejection. The change in impedance caused by respiration can be removed using electronic filtering techniques because it is of larger magnitude and lower frequency. The cardiac output sensor 146 in the embodiment of FIG. 2 is manufactured by CardioDynamics, 6175 Nancy Ridge Drive, San Diego, Calif. 92121.

The following tables describe exemplary parameters which pertain to cardiac output and which are measured (Table 1) or calculated (Table 2) by the monitoring system 100.

TABLE 1

Measured Parameters

| Label | Parameter | Definition | Normal Ranges | Derivation/Formula |
|---|---|---|---|---|
| TFC | Thoracic Fluid Content | The electrical conductivity of the chest cavity, which is primarily determined by the intravascular, intraalveolar, and the interstitial fluids in the thorax. | Males 30–50/kohm Females: 21–37/kohm | $TFC = \frac{1}{TFI}$ |
| ACI | Acceleration Index | Initial acceleration of blood flow in the aorta, which occurs within the first 10 to 20 milliseconds after the opening of the aortic valve. | Males: 70–150/100 sec² Females: 90–170/100 sec² | $ACI = \frac{d^2Z/d^2t\,MAX}{TFI}$ |
| VI | Velocity Index | Peak velocity of blood flow in the aorta. | 35–65/1000 sec | $VI = \frac{dZ/dt\,MAX}{TFI}$ |
| HR | Heart Rate | Number of heart beats each minute. | 60–100 bpm | HR = Beats per minute |

TABLE 2

Calculated Parameters

| Label | Parameter | Definition | Normal Ranges | Derivation/Formula |
|---|---|---|---|---|
| CO | Cardiac Output | Amount of blood pumped by the left ventricle each minute | 4.0–8.0 l/min | CO = HR · SV |
| CI | Cardiac Index | Cardiac output normalized for body surface area. | 2.5–4.5 l/min/m$^2$ | $CI = \frac{CO}{BSA}$ |
| SV | Stroke Volume | Amount of blood pumped by the left ventricle each heartbeat. | 60–130 ml | SV = VEPT · LVET · VI |
| SI | Stroke Index | Stroke volume normalized for body surface area. | 35–65 ml/m$^2$ | $SI = \frac{SV}{BSA}$ |
| SVR | Systemic Vascular Resistance | The resistance to the flow of blood in the arterial system (often referred to as "afterload"). | 900–1400 dynes sec/cm$^5$ | $SVR = 80 \cdot \frac{(MAP - CVP)}{CO}$ |
| SVRI | Systemic Vascular Resistance Index | The resistance to the flow of blood in the arterial system normalized for body surface area. | 1900–2400 dynes sec m$^2$/cm$^5$ | $SVRI = 80 \cdot \frac{(MAP - CVP)}{CI}$ |
| LVSWI | Left Ventricular Stroke Work Index | The work performed by the left ventricle to eject the stroke volume into the aorta. | 40–60 gm m/m$^2$ | LVSWI = (MAP − PAWP) · SI · 0.0136 |
| LCWI | Left Cardiac Work Index | An indicator of the amount of work the left ventricle must perform to pump blood each minute, normalized for body surface area. | 3.0–5.5 kg m/m$^2$ | LCWI = (MAP − PAWP) · CI · 0.0144 |
| STR | Systolic Time Ratio | The ratio of the electrical and mechanical systole. | 0.30–0.50 | $STR = \frac{PEP}{LVET}$ |
| eDO$_2$I | Estimated Delivered Oxygen Index | The rate of oxygen transport in the arterial blood. | Dependent on clinical pathology | DO$_2$I = CI · SpO$_2$ · 1.38 · Hb · 10 (estimated value) |
| PEP | Pre Ejection Period | The time interval from the beginning of electrical stimulation of the ventricles to the opening of the aortic valve (electrical systole). | Depends on HR preload and contractility | Time interval from beginning of Q wave on the ECG to the B point on the dZ/dt waveform |
| LVET | Left Ventricular Ejection Time | The time interval from opening to the closing of the aortic valve (mechanical systole). | Depends on HR preload and contractility | Time interval from the B point to the X point on the dZ/dt waveform |

In Table 2, VEPT is volume of electrically participating tissue (volume conducted for size of thorax affected by height, weight, and sex), TFL is thoracic fluid index, which is the baseline thoracic impedance, $Z_0$, dZ/dtMAX is maximum of the first derivative of $\Delta Z$, $d^2Z/d^2tMAX$ is maximum of the second derivative of $\Delta Z$, BSA is body surface area, CVP is central venous pressure, PAWP is pulmonary artery wedge pressure, B point is opening of aortic valve, and X point is closing of aortic valve. MAP (mean arterial pressure or the mean pressure that comes from an arterial or femoral invasive blood pressure reading), PAWP, SpO2 (pulse oximetry), and Hb (hemoglobin) are hemodynamic input data used for calculation of individual cardiac output parameters. The parameters in Table 2 are calculated by the analysis module 175.

Figure 3:
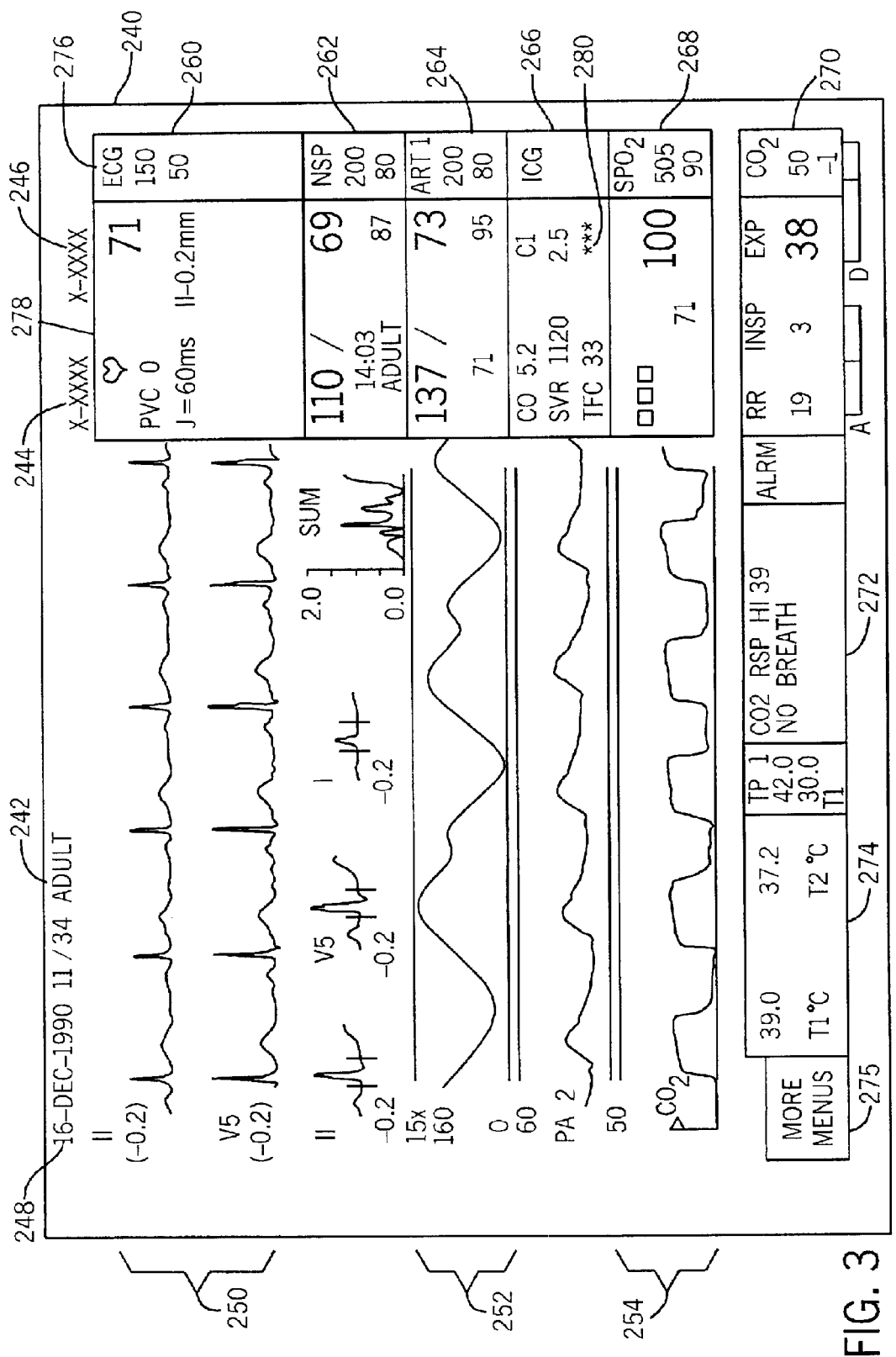
FIG. 3 is a top level menu displayed by a display of the patient monitoring system of FIG. 1.

Referring now to FIGS. 3–19, an operator interface that assists monitoring and displaying cardiac output information is shown. Referring first to FIG. 3, a top level screen display 240 is shown. The screen display 240 comprises a plurality of information fields, a plurality of waveforms, and a plurality of parameter windows. The information fields include a field 242 that displays care unit, a field 244 that displays bed number, a field 246 that displays patient name, and a field 248 that displays date and time. The plurality of waveforms include ECG waveforms 250, cardiac output waveform 252, a CO2 waveform 254, and other waveforms.

The parameter windows are displayed on the far right of the screen display and, when necessary, across the bottom. The number of parameter windows that are displayed depends on the number of sensors connected to the patient monitoring system 100. Preferably, every monitored parameter has a parameter window. In FIG. 3, the parameter windows include an ECG window 260, an NBP (non-invasive blood pressure) window 262, an ART (blood pressure from an invasive arterial blood pressure reading) window 264, an ICG (impedance cardiography or cardiac output) window 266, an SP02 window 268, a CO2 (carbon dioxide) window 270, an alarm window 272, and a temperature window 274. Parameter labels may be displayed in different sizes depending on the display layout and the number of parameters being monitored. The parameter windows may be double high sized (as with the ECG parameter window 260), normal size, (as with the remaining parameter windows 262–274), or reduced size (not shown). Each parameter window has two parts: a parameter label portion 276 and a measured value portion 278. Each parameter window 260–274 displays one primary parameter and three secondary parameters. Limits and units of measure may also be displayed under the parameter label.

For example, the ICG parameter window 266 displays four of the sixteen parameters identified in Tables 1 and 2 along with a signal quality 280 indicator for the impedance waveform 252. The ICG parameter window 266 has one large primary subparameter value and three other secondary subparameters, all of which are selectable for display. The selectable subparameters may be any of those in Tables 1 and 2. The signal quality indicator 280 comprises one to three asterisks which reflect the confidence in the value correctness: Three asterisks is high confidence, two asterisks is average confidence, and one asterisk is low confidence. During normal monitoring, values in the parameter window 266 updates periodically (e.g., every two seconds).

The main operator control is preferably a dial input device. The dial input device rotates in either direction to highlight parameter labels and menu options. After highlighting the desired selection, the dial input device may be pressed by the operator to view a new menu or a small pop-up menu. Thus, from the main menu shown in FIG. 3, the operator accesses a parameter menu by selecting the appropriate parameter label using the dial input device. The operator can also access other menus (not related to a specific parameter) by selecting the more menus option.

Figure 4:
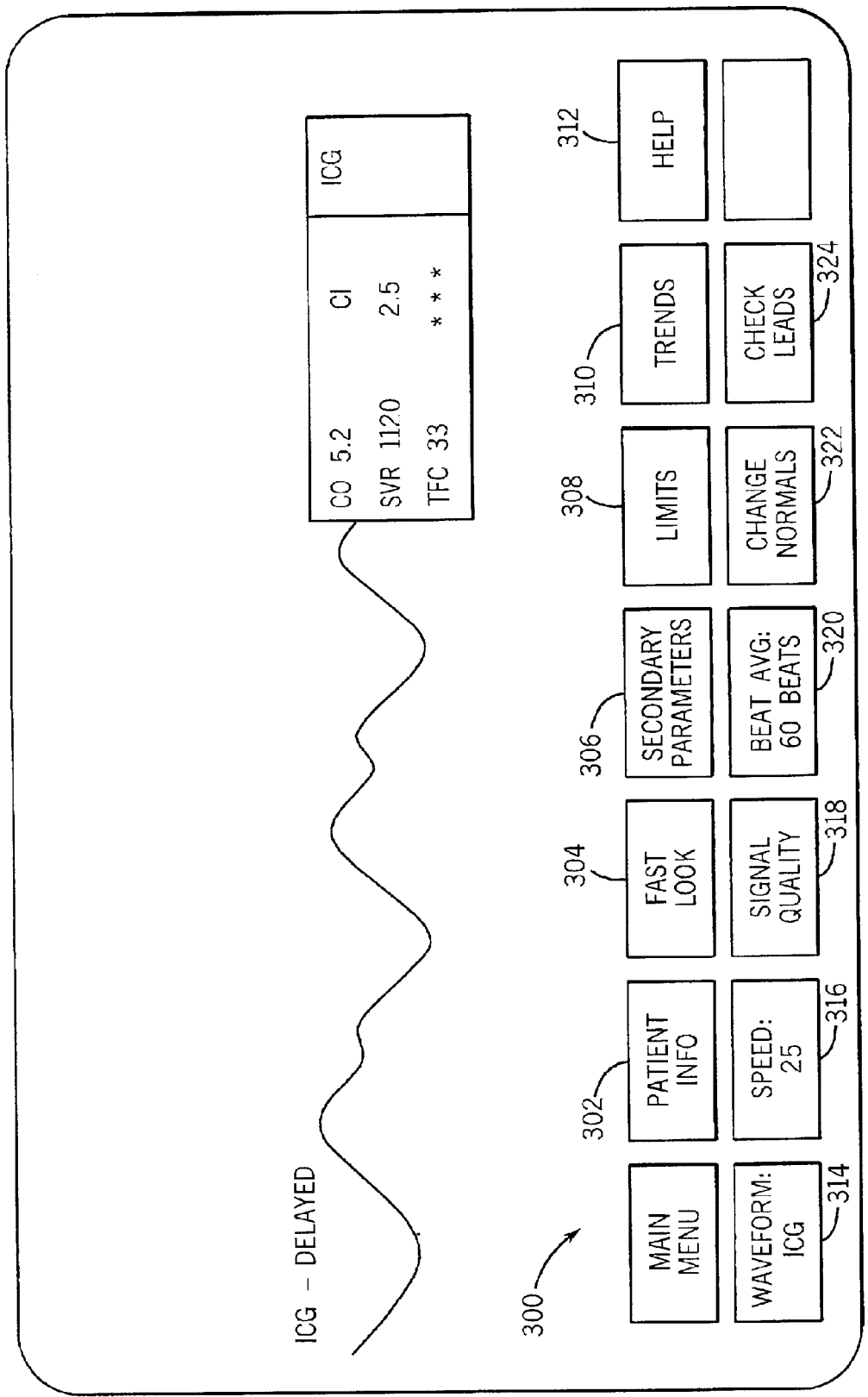
FIG. 4 is a top level cardiac output menu displayed by the display of the patient monitoring system of FIG. 1.

When the ICG window 266 is highlighted and the operator pushes the dial input device, a top level ICG menu 300 as shown in FIG. 4 is displayed. The top level ICG menu 300 comprises a patient information button 302, a fast look button 304, a secondary parameters button 306, a limits button 308, a trends button 310, a help button 312, a waveform button 314, a speed button 316, a signal quality button 318, a beat average button 320, a change normals button 322, and a check leads button 324.

All available menu options appear with the current selection being highlighted. In some instances, arrows are also highlighted, indicating that the dial input device can be rotated (or scrolled) to change the selection. When the dial input device is rotated, the new selection is highlighted and the operator is permitted to press the dial input device to select a particular menu option (i.e., button). If the data entry device 115 is a touch screen integrated with the video display 202, then the buttons 302–324 may be activated by the operator by pressing the appropriate location on the video display 202. Preferably, however, the buttons 302–324 merely appear as buttons and instead are activated by the dial input device.

Figure 5:
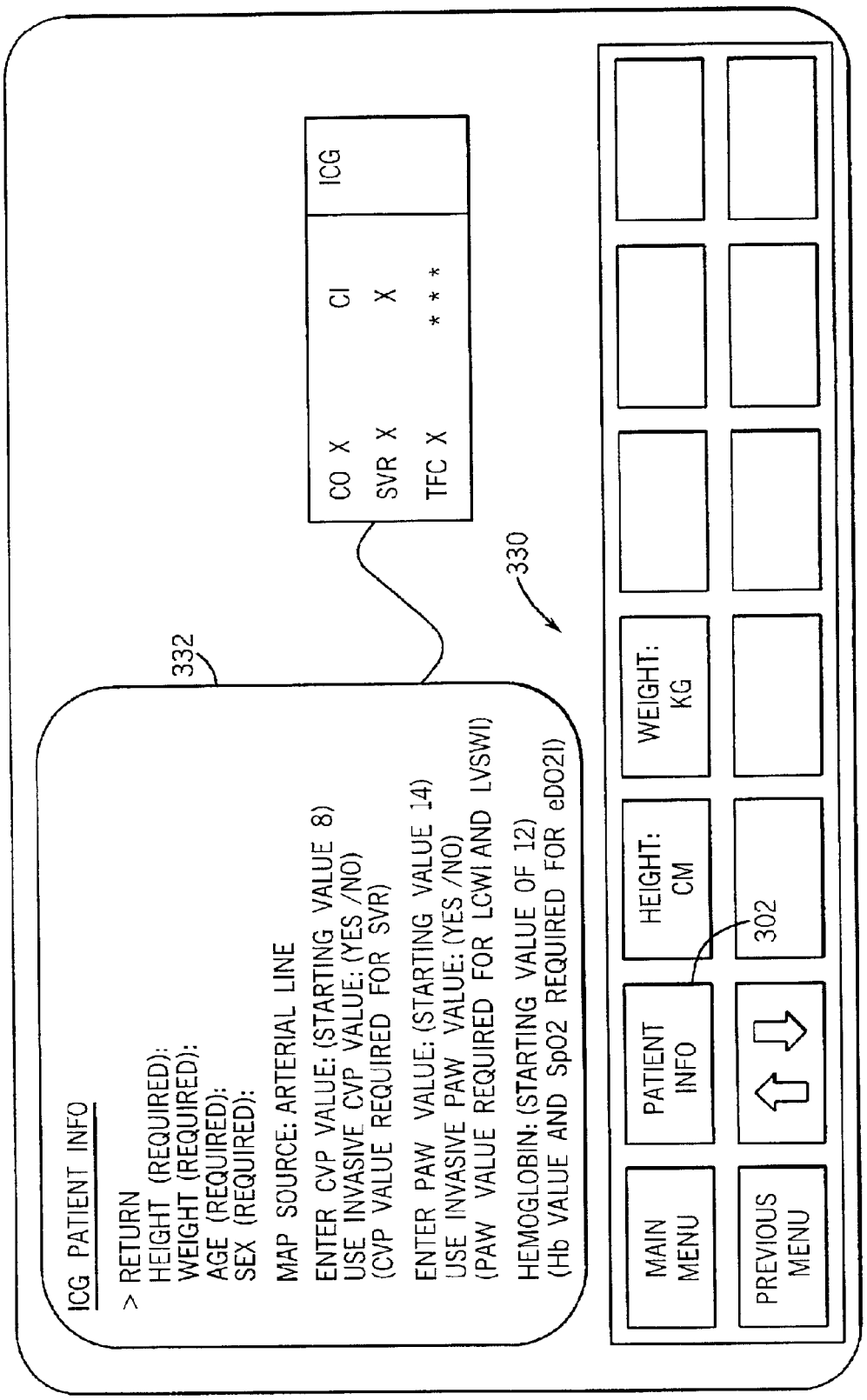
FIG. 5 is a patient information menu displayed by the display of the patient monitoring system of FIG. 1.

When an operator input is received selecting the patient info button 302, a patient info menu 330 is displayed as shown in FIG. 5. The patient info menu 330 includes an information display window 332 which prompts an operator to enter patient information. There are four primary patient demographic values used for cardiac output monitoring: height, weight, sex, and age. Additional information is used for monitoring specific parameters. The information display window 332 prompts an operator to choose an option for MAP source (e.g., either non-invasive blood pressure or arterial line). The information display window 332 also prompts the operator to manually enter a value for CVP or alternatively to permit the system 100 to use an invasive CVP value. The information display window 332 also prompts the operator to enter a PAW (pulmonary artery wedge pressure) value or alternatively to permit the system 100 to use the invasive PAW sensor as the source of this information. Finally, the information display window 332 prompts the operator to enter an Hb (hemoglobin) value. The information window 332 is superimposed over the upper left portion of the screen display. Information windows are displayed when a help option is selected with certain menu options, as described below. The information window contains instructions or other non-real time information.

Figure 6:
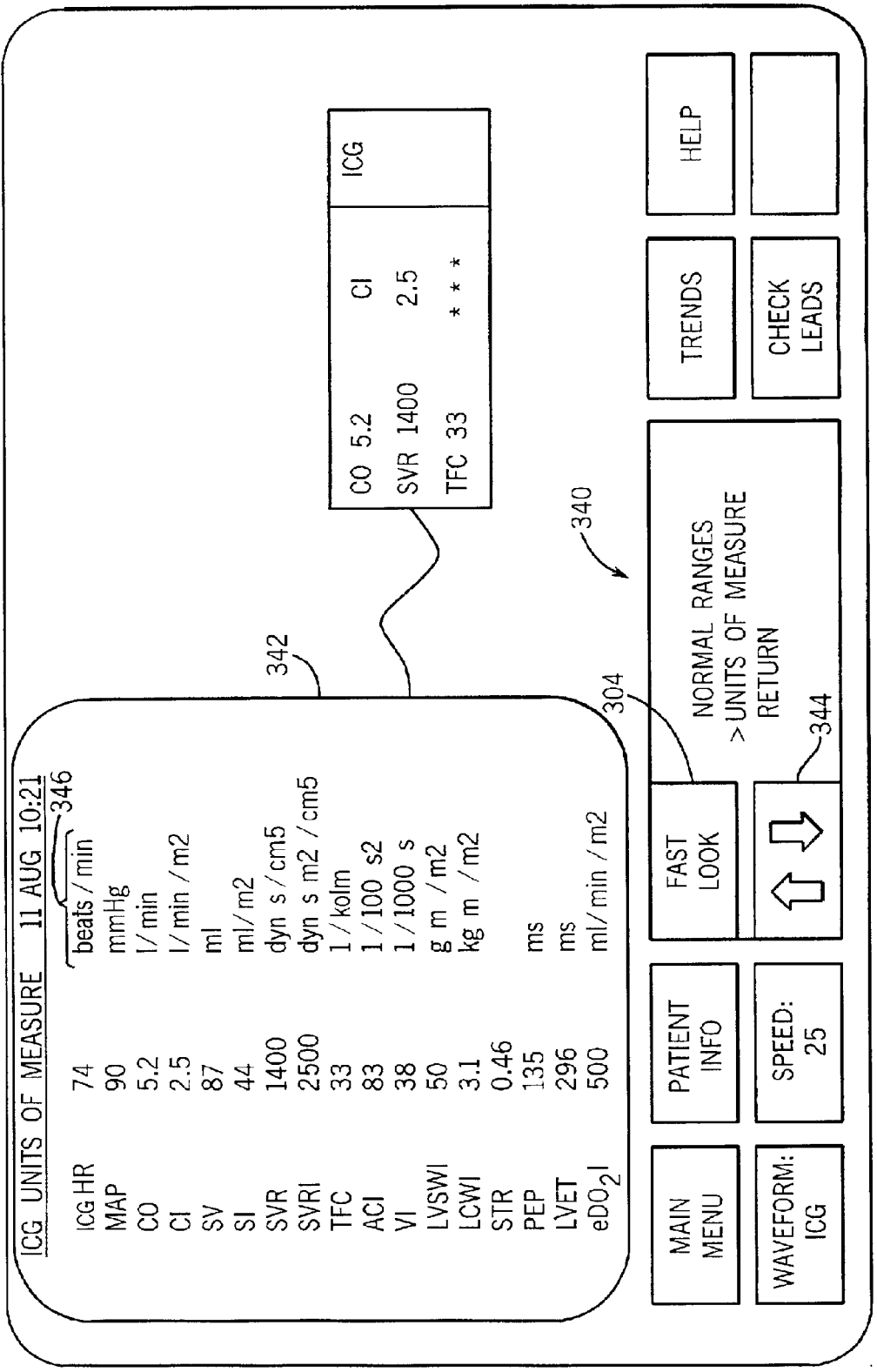
FIG. 6 is a fast look menu displayed by the display of the patient monitoring system of FIG. 1, in which cardiac output data is displayed in a units of measure format.

If an operator input is received selecting the fast look button 304, then a fast look menu 340 is displayed to the operator as shown in FIG. 6. The fast look menu 340 allows the operator to quickly view a comprehensive list of cardiac output parameter data in an information window 342.

As previously noted, the arrows 344 indicate that the dial input device can be rotated to change the selection between normal ranges, units of measure, and return. The change is implemented when the dial input device is pressed. Thereafter, the pop-up menu closes and the change is in effect.

Figure 7:
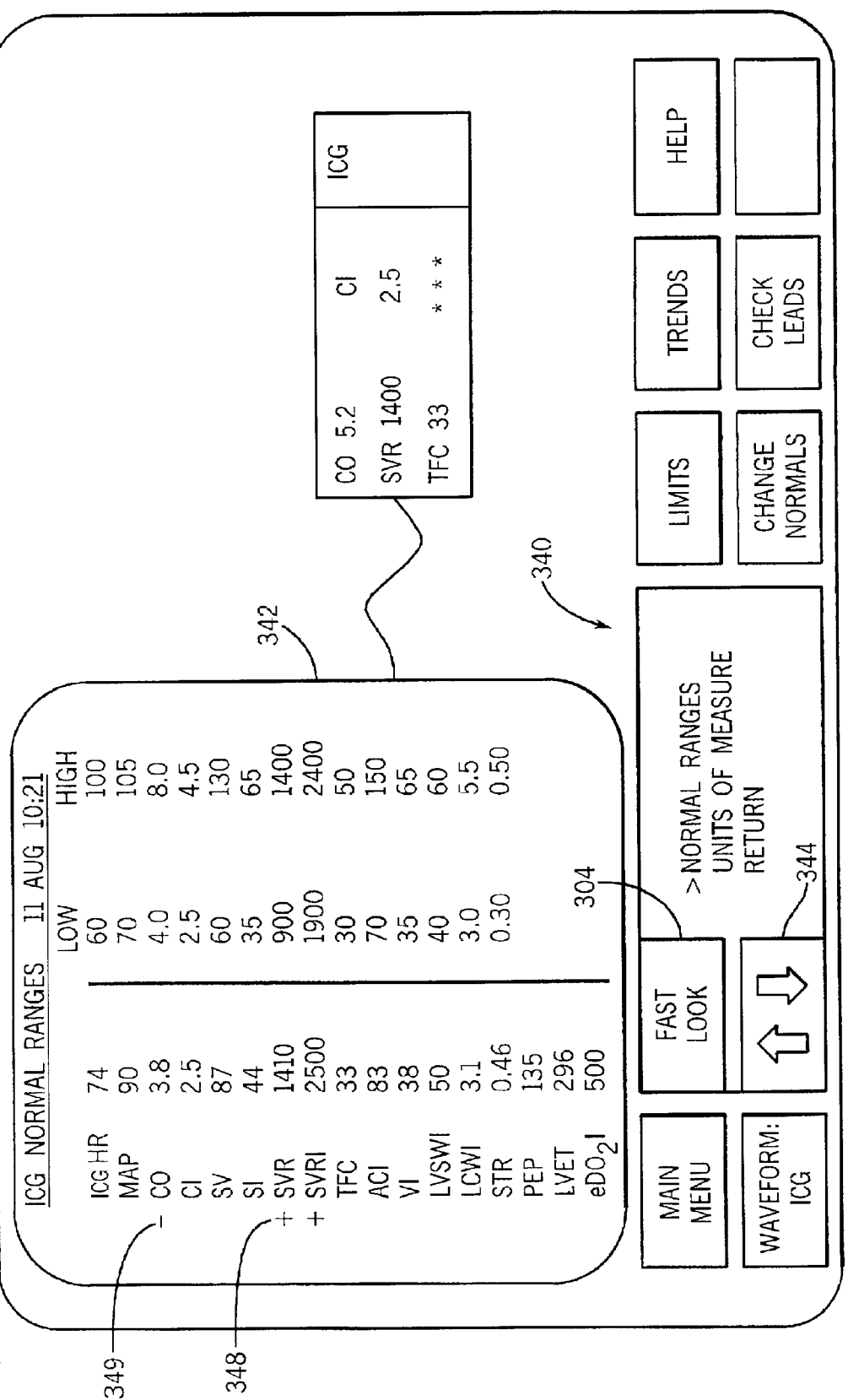
FIG. 7 is a fast look menu displayed by the display of the patient monitoring system of FIG. 1, in which cardiac output data is displayed in a normal ranges format.

In FIG. 6, the cardiac output data is displayed in "units of measure" format in the information display window 342, in which the cardiac output data is displayed along with units of measure in a region 346 of the information display window 342. The cardiac output data may also be stored in a "normal ranges" format in which the information display window 342 displays the ICG data along with normal ranges as shown in FIG. 7. A plus (+) 348 or minus (−) 349 is used to indicate data that falls outside of the specified ranges.

Figure 8:
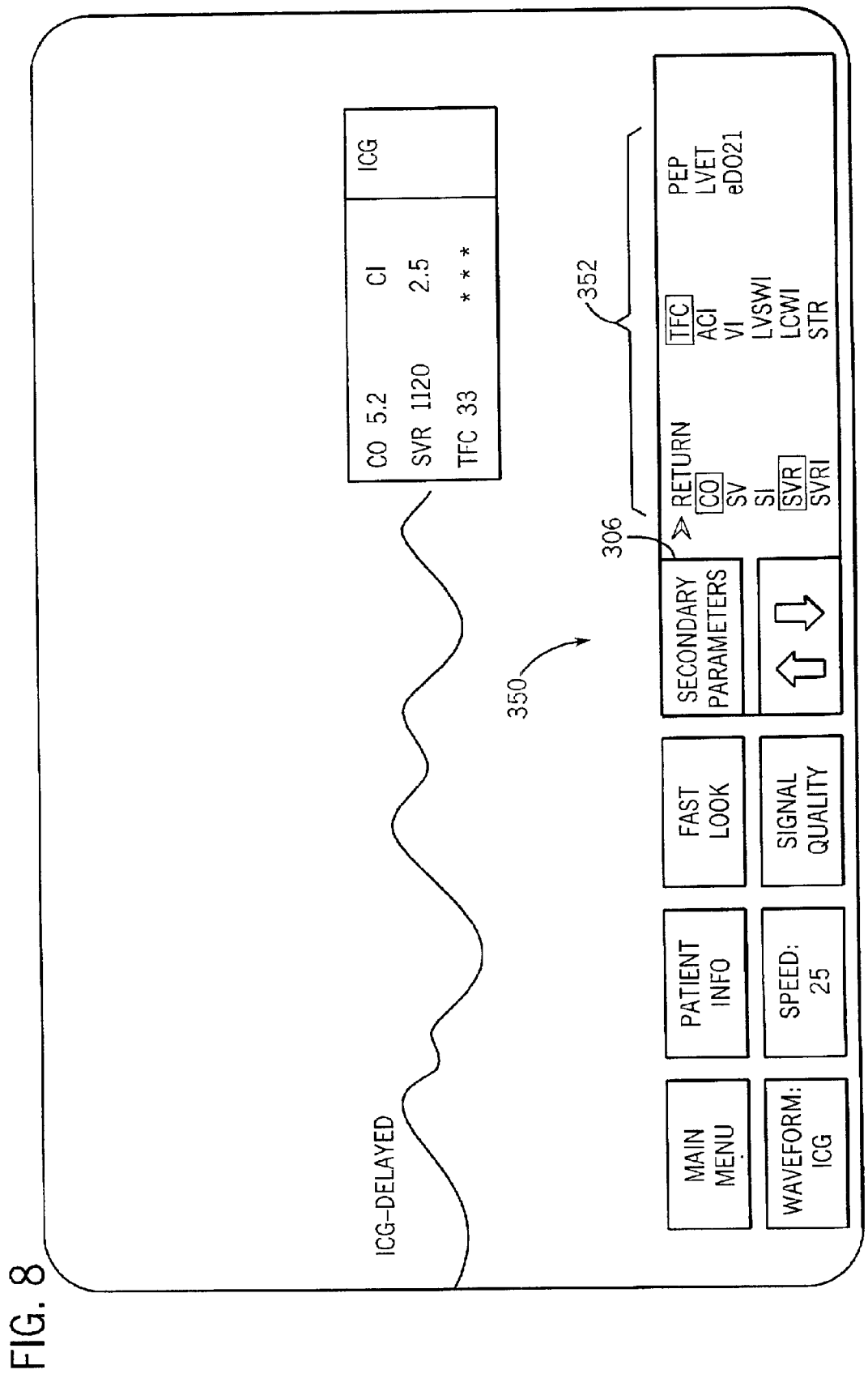
FIG. 8 is a secondary parameters menu displayed by the display of the patient monitoring system of FIG. 1.

If an operator input is received selecting the secondary parameters button 306, then a secondary parameters menu 350 is displayed as shown in FIG. 8. The secondary parameters menu 350 permits the operator to select which parameters are to be displayed as secondary parameters in the ICG parameter window 266. Three secondary parameters from Tables 1 and 2 are set forth in a displayed list 352 and can be selected for display in the parameter window 266. The menu 350 permits the operator to select three choices from the parameter list, and these choices are then displayed in the parameter window 266. The parameter that has been assigned to the primary parameter position is not included in the list of parameters available for secondary parameter display.

Figure 9:
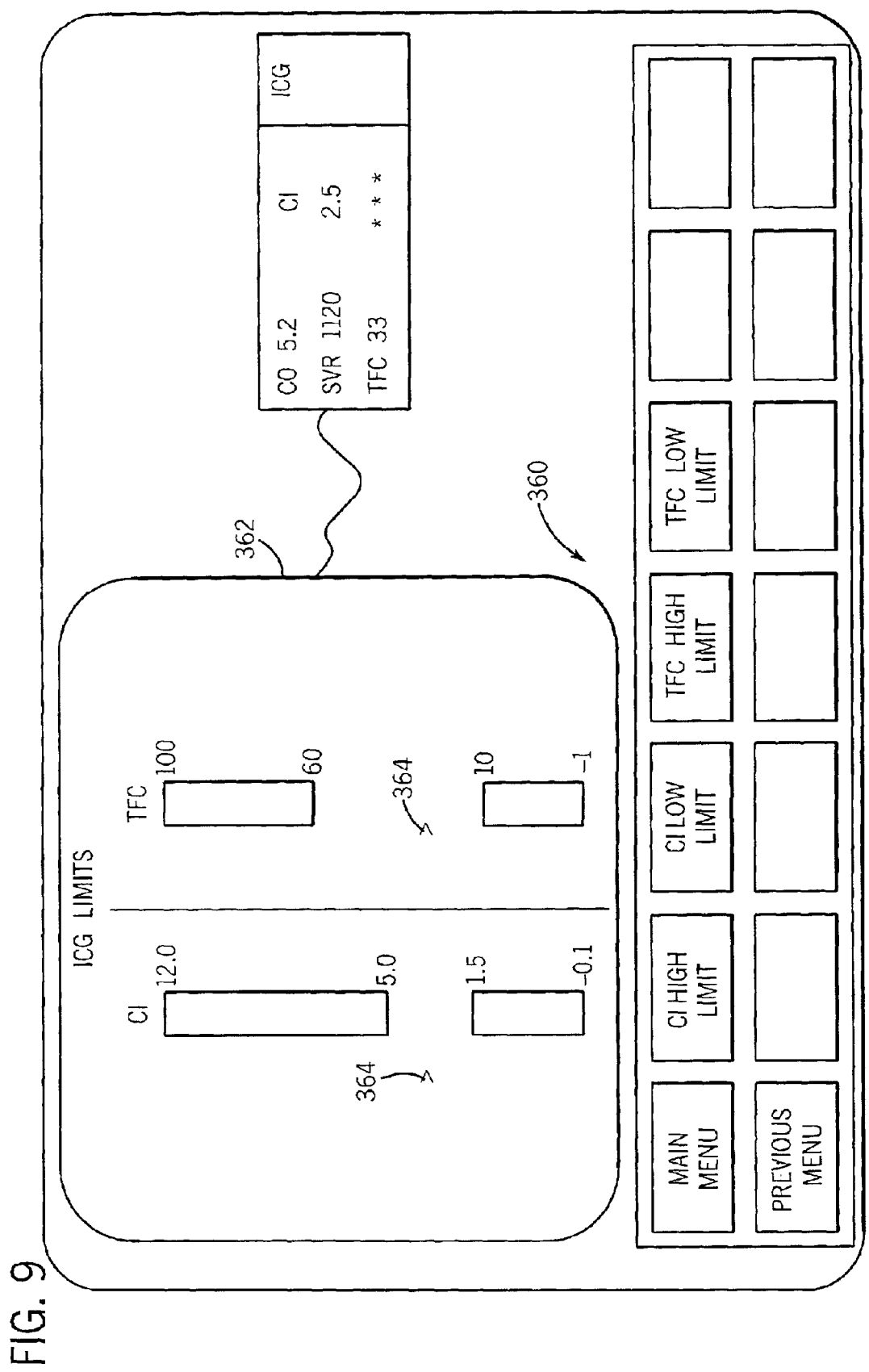
FIG. 9 is a limits menu displayed by the display of the patient monitoring system of FIG. 1.

If an operator input is received selecting the limits button 308, then a limits menu 360 is displayed as shown in FIG. 9. The limits menu permits the operator to adjust alarm limits for TFC and Cl. High and low limits can be adjusted for both parameters. The current limit settings are shown in an information window 362, and the current value of that parameter for the monitored patent is also shown using arrows 364. As long as that value remains between the high and low limits, there will be no alarm. Should a limit be exceeded, an alarm will occur.

If an operator input is received selecting the trends button 310, then trending information for the cardiac parameters is displayed in tabular or graphical format. A trend is a graphic representation of one parameter over a specified period of time. Every non-episodic parameter is sampled 30 times a minute. A median value is determined and that value is stored for trend display at one-minute resolution. Episodic parameters (NBP, etc.) are stored every time one occurs. Any combination of parameters may be trended as determined by operator inputs. The cardiac output information in Tables 1 and 2 can be trended along with ECG data and all of the other information collected by the sensors 141–146 and 155.

Figure 10:
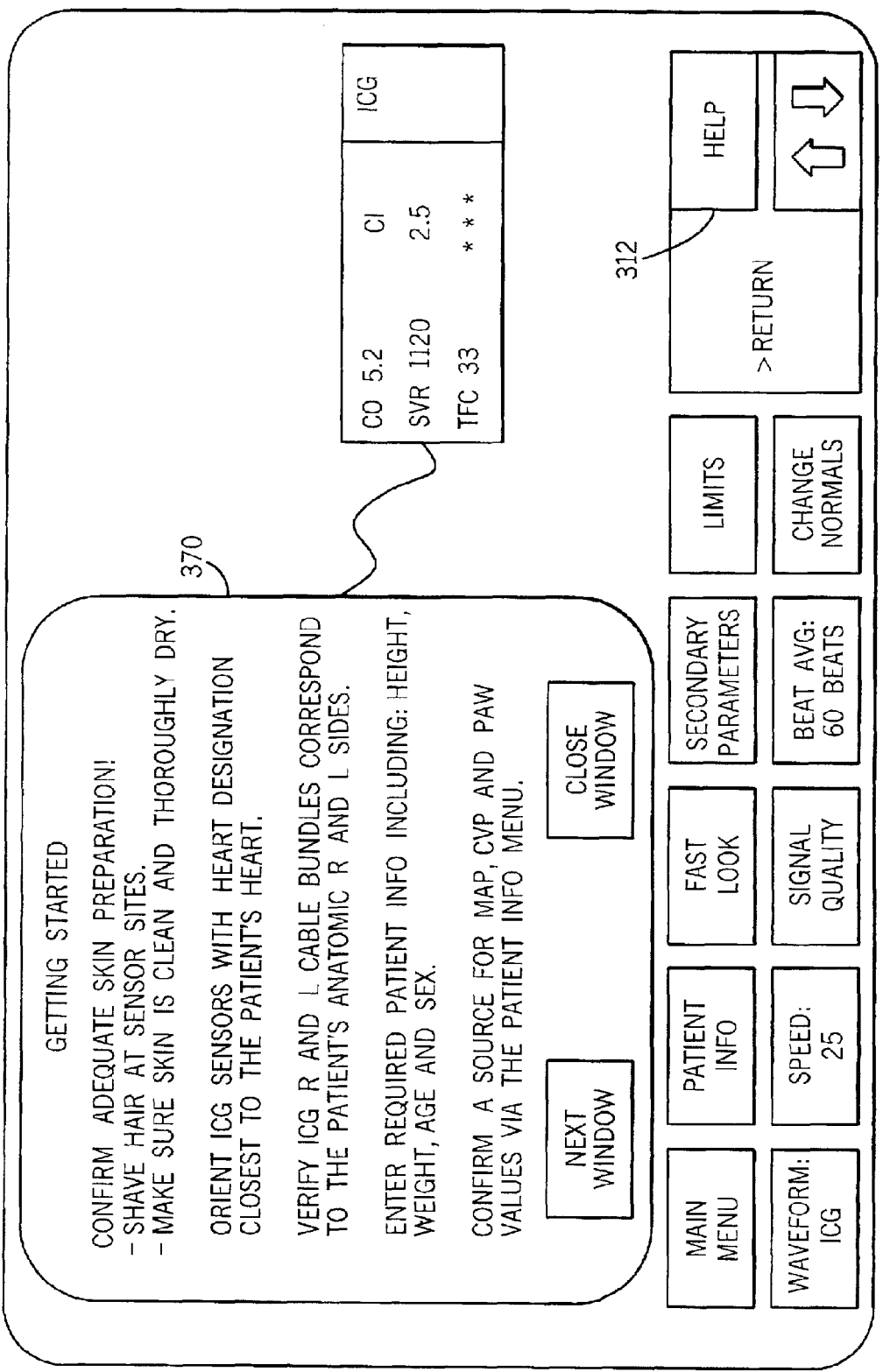
FIGS. 10–12 are help menus with different help information windows displayed by the display of the patient monitoring system of FIG. 1.
Figure 11:
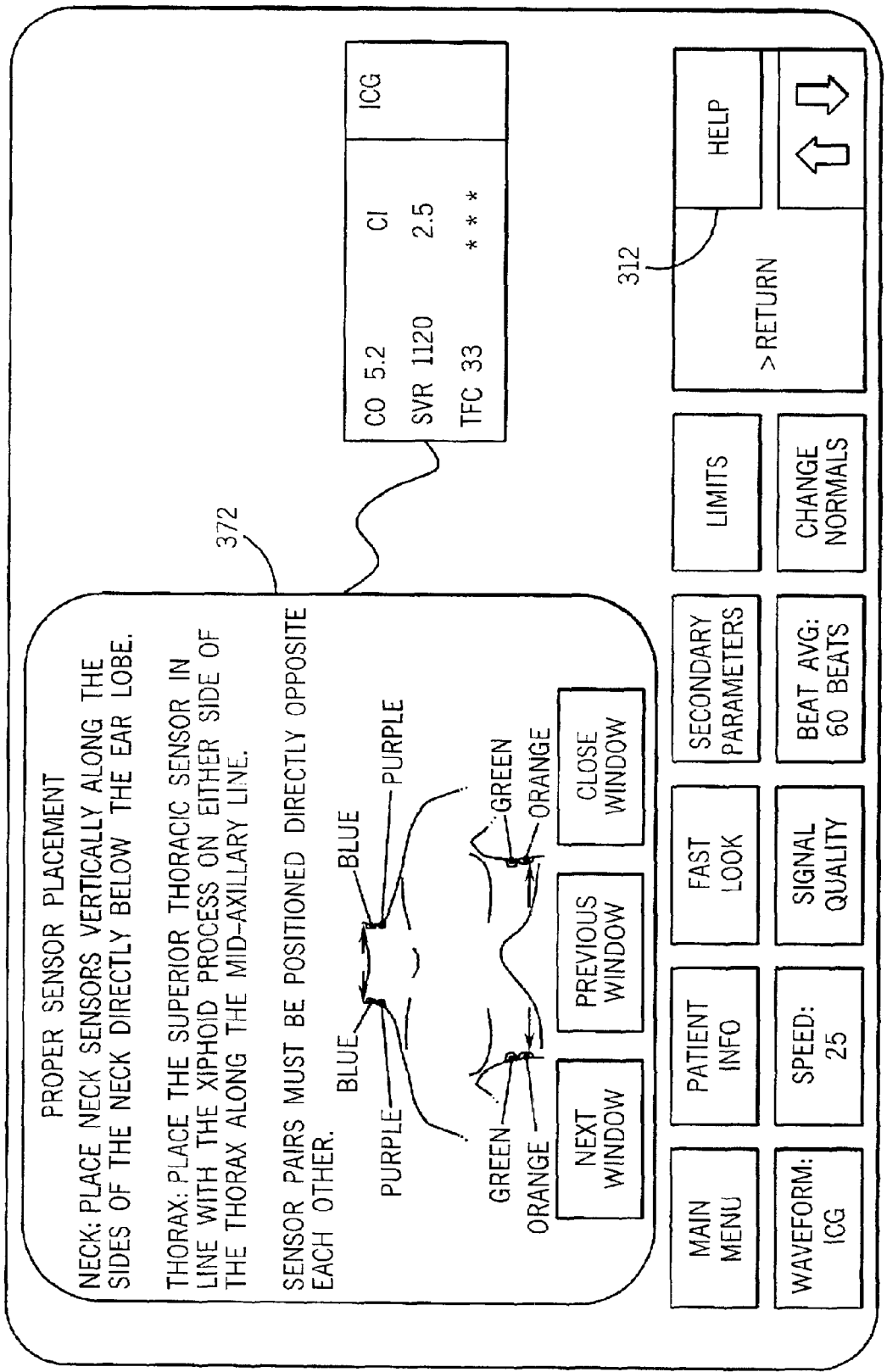
Figure 12:
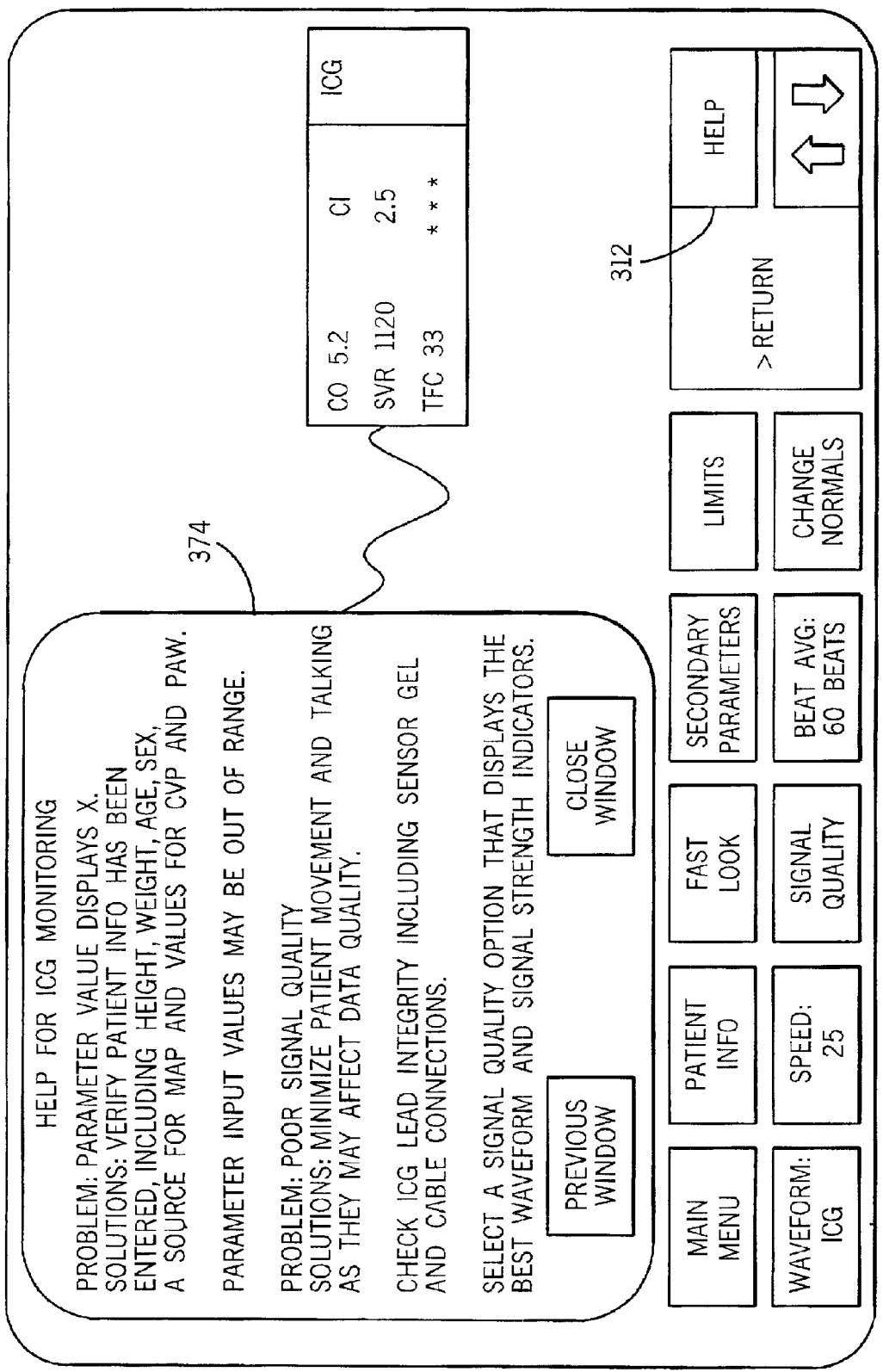

If an operator input is received selecting the help button 312, then the help information windows 370, 372, 374 are displayed as shown in FIGS. 10–12. Three help information windows 370, 372, 374 provide information for cardiac output setup and monitoring. Topics include skin preparation (window 370, FIG. 10), proper sensor placement (window 372, FIG. 11), and troubleshooting issues (window 374, FIG. 12).

Figure 13:
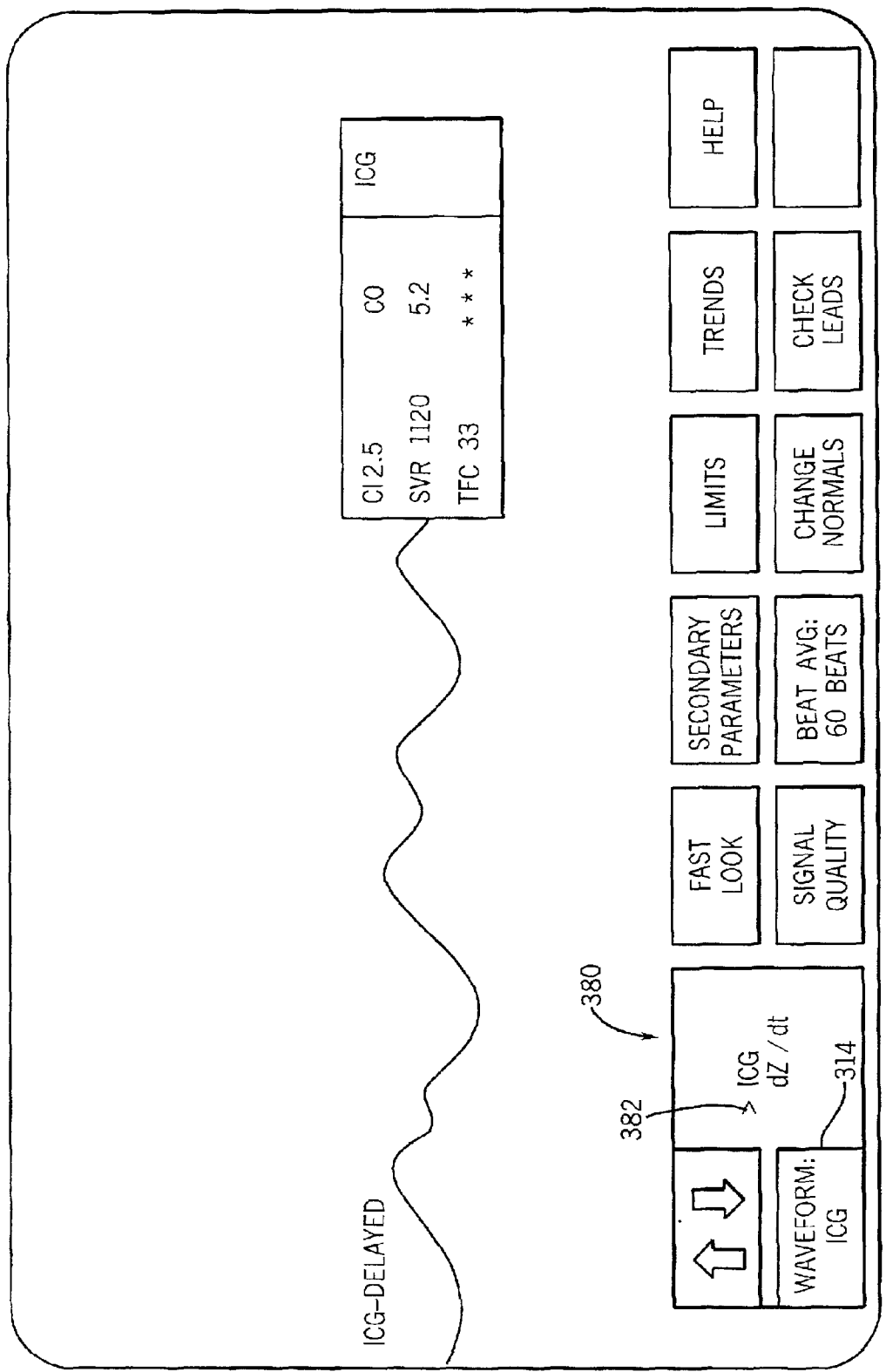
FIG. 13 is a waveform menu displayed by the display of the patient monitoring system of FIG. 1.

If an operator input is received selecting the waveform button 314, then a waveform menu 380 is displayed as shown in FIG. 13. The waveform menu 380 provides the operator with the option of selecting a waveform which reflects beat-to-beat changes in impedance consistent with the events of the cardiac cycle, or a dZ/dt waveform which reflects the rate of change in the impedance waveform. The selected waveform 252 is labeled in the waveform area on the display 240. The cardiac output waveform 252 can be turned on or off using the waveform menu 380. In FIG. 13, the displayed waveform is the impedance waveform, as indicated by arrow 382.

Figure 14:
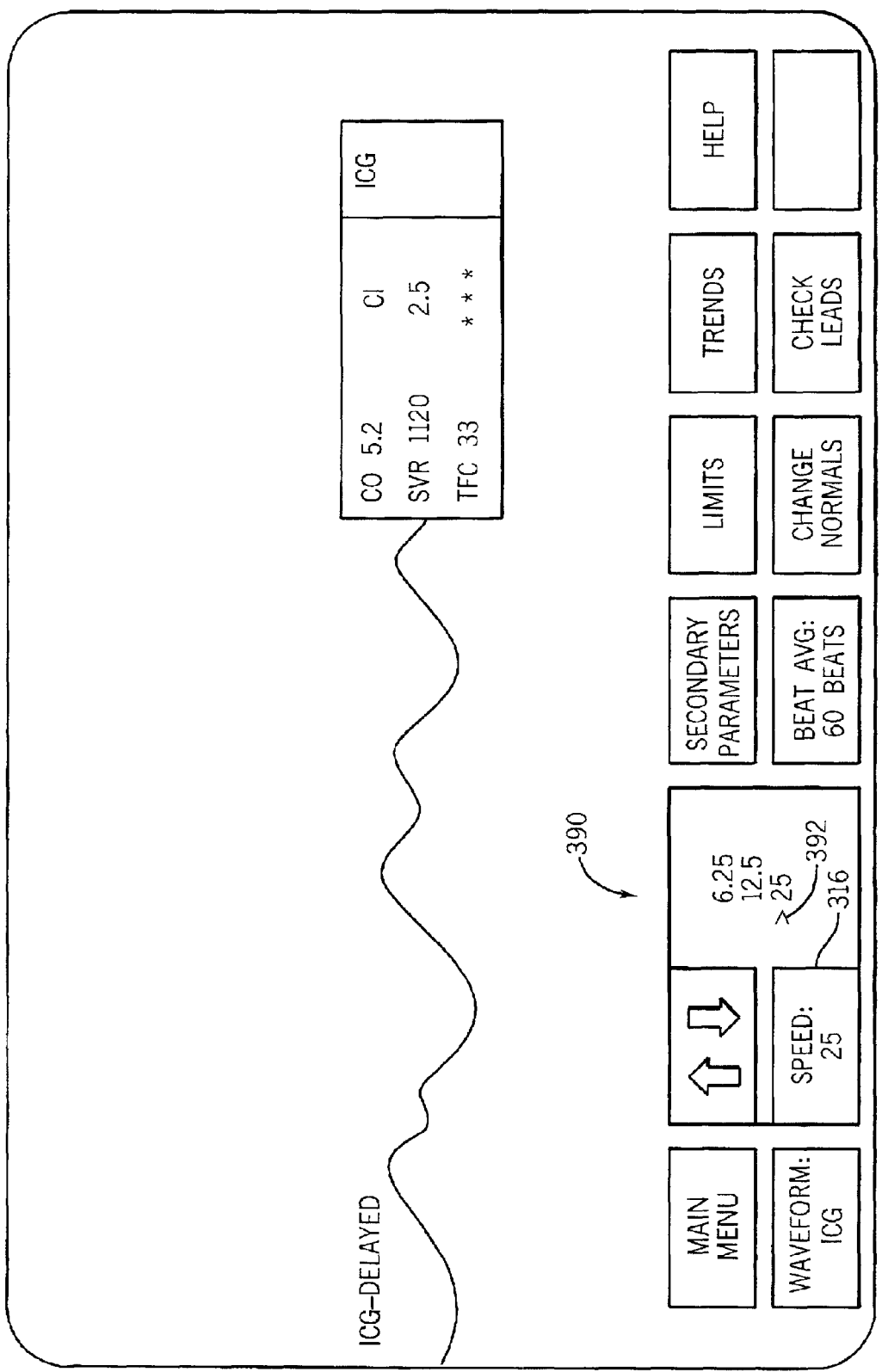
FIG. 14 is a speed menu displayed by the display of the patient monitoring system of FIG. 1.

If an operator input is received selecting the speed button 316, then a speed menu 390 is displayed as shown in FIG. 14. The speed menu 390 is used to select a sweep speed for the displayed cardiac output waveform 252. In FIG. 14, the speed selected is 25 mm/sec as indicated by arrow 392.

Figure 15:
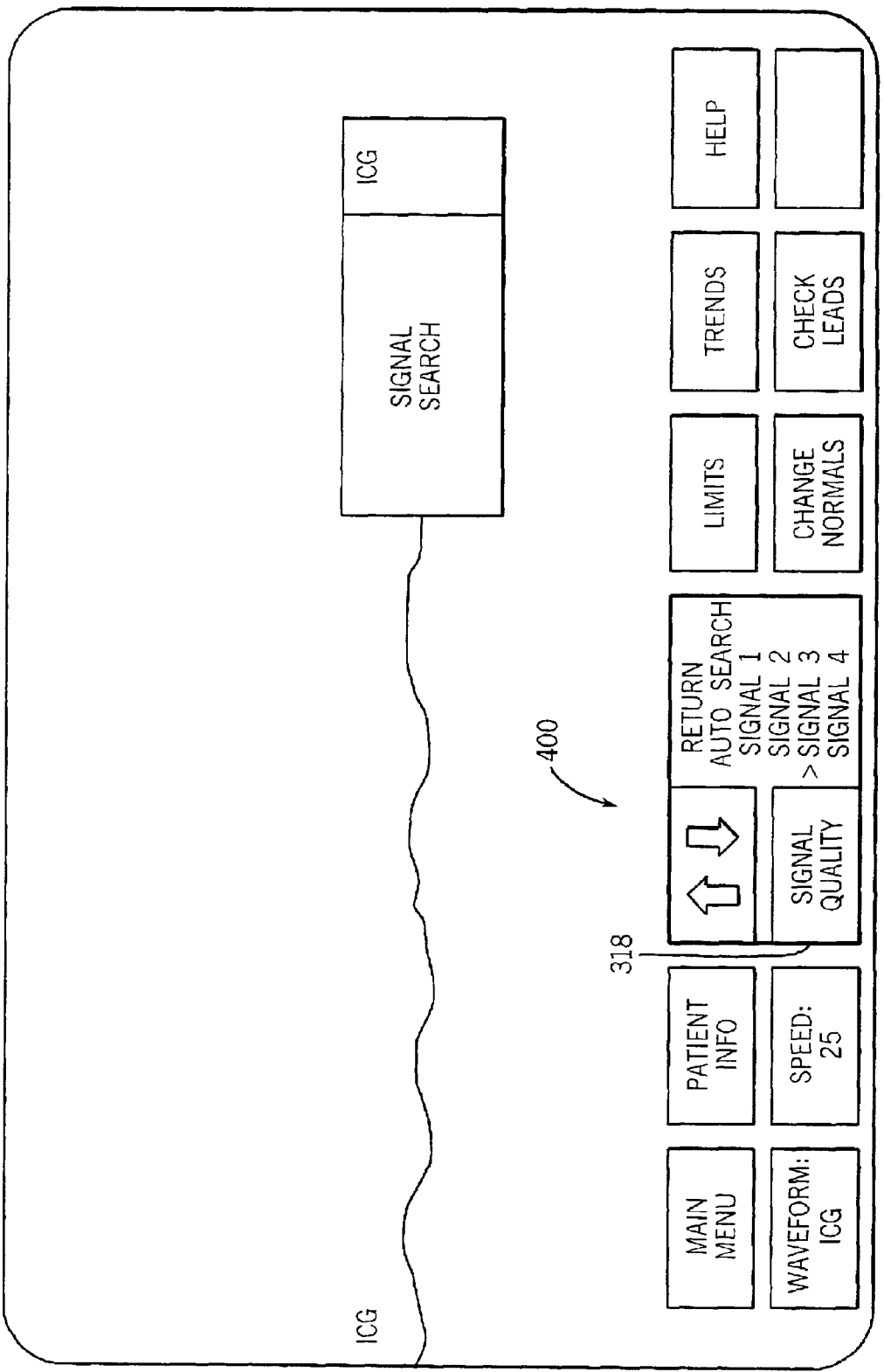
FIG. 15 is a signal quality menu displayed by the display of the patient monitoring system of FIG. 1.

If an operator input is received selecting the signal quality button 318, then a signal quality menu 400 is displayed as shown in FIG. 15. Upon start-up, the analysis module 175 selects what is considered to be the best signal for optimum data acquisition and processing. The signal quality menu 400 allows the operator to manually override this process. The menu 400 provides the operator with choices including auto search and signal 1 through signal 4. If the operator selects auto search, the system 100 searches for a new optimal signal. If the operator selects signal 1 through signal 4, the system 100 uses the selected signal.

Figure 16:
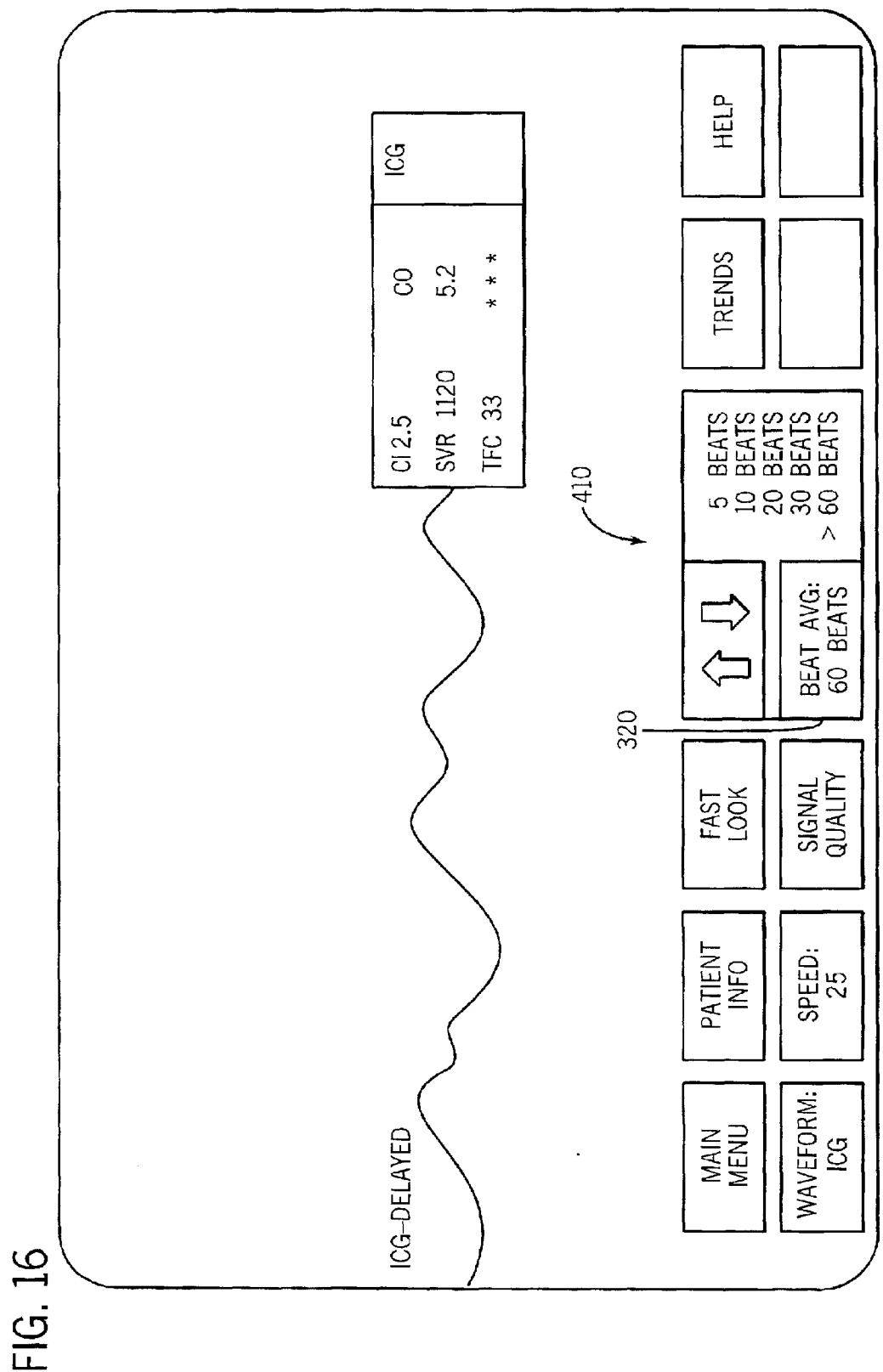
FIG. 16 is a beat average menu displayed by the display of the patient monitoring system of FIG. 1.

If the operator selects the beat average button 320, then a beat average menu 410 is displayed as shown in FIG. 16. The beat average menu 410 permits the operator to select the number of beats that are averaged for data update. Beat average choices are 5, 10, 20, 30, and 60 beats. The smaller the number of beats average, the more likely it is that the data will be affected by artifact. A high number of beats averaged smoothes out the acquired data with a minimum of fluctuation.

Figure 17:
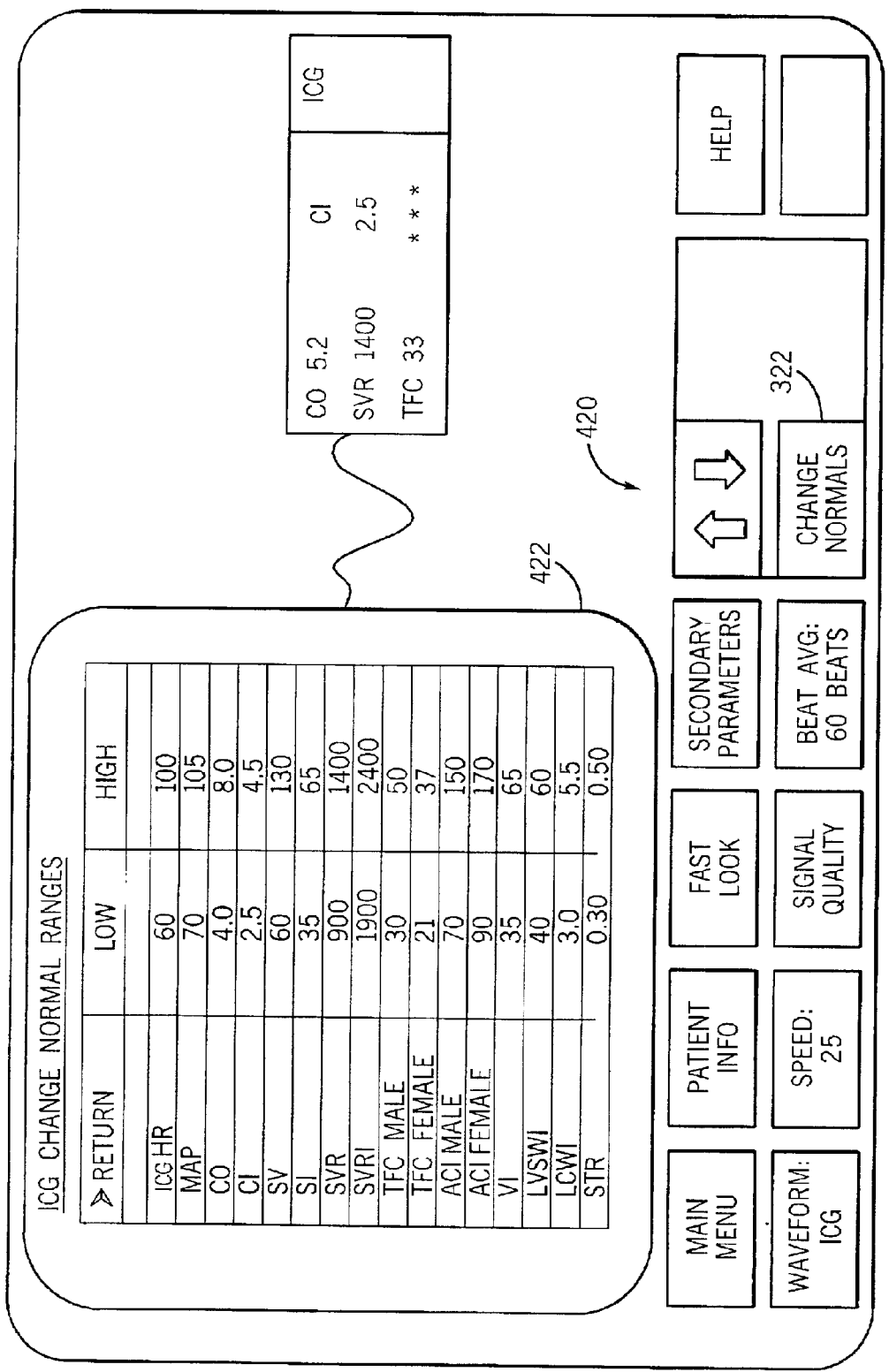
FIG. 17 is a change normals menu displayed by the display of the patient monitoring system of FIG. 1.

If the operator selects the change normals button 322, then a change normals menu 420 is displayed as shown in FIG. 17. The change normals menu 420 permits the operator to change the normal ranges for cardiac flow parameters. Default normal ranges are displayed in an information window 422. Default normal ranges may be changed in accordance with the medical judgment of the attending physician.

Figure 18:
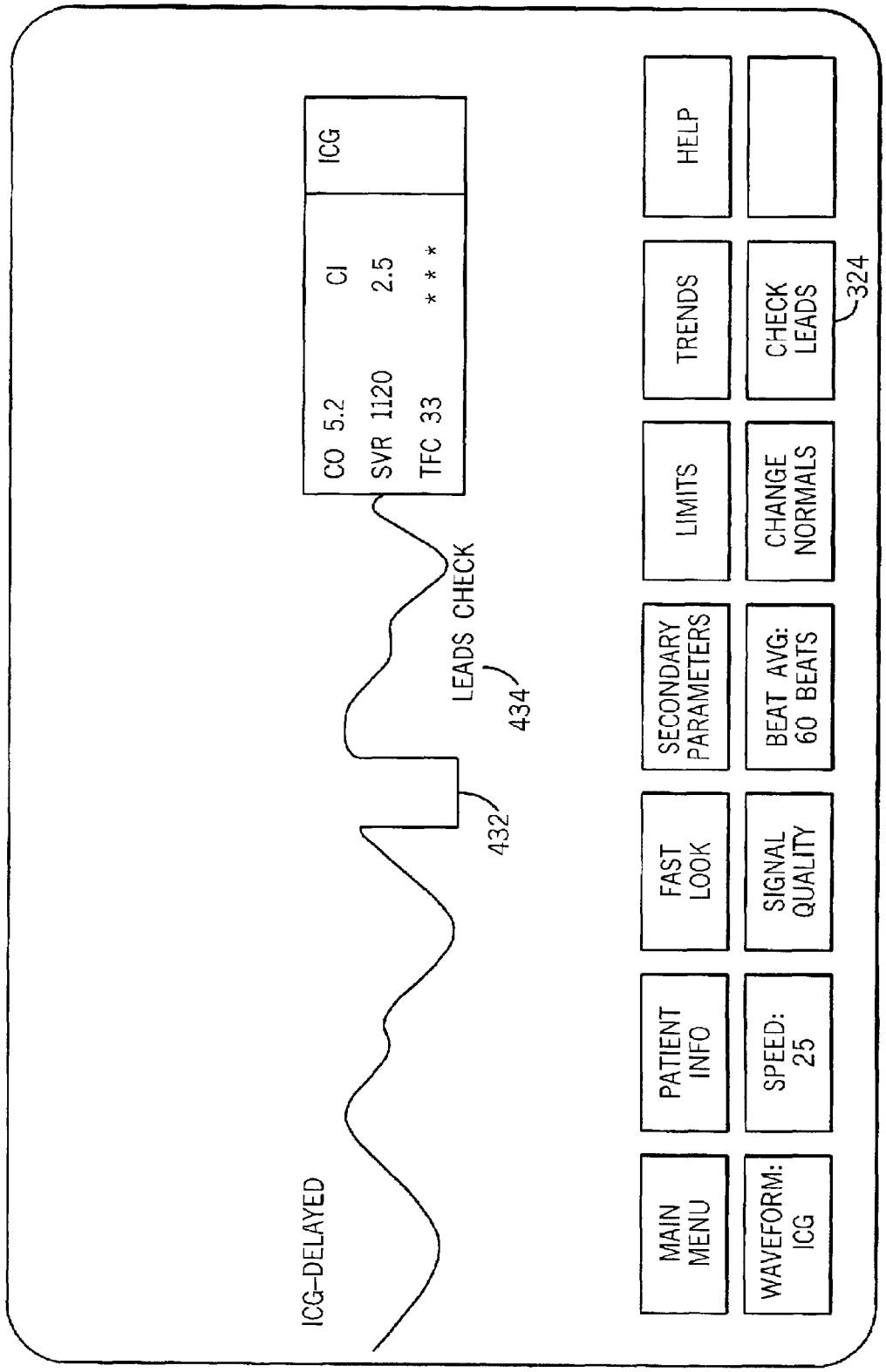
FIG. 18 is a check leads menu displayed by the display of the patient monitoring system of FIG. 1.
Figure 19:
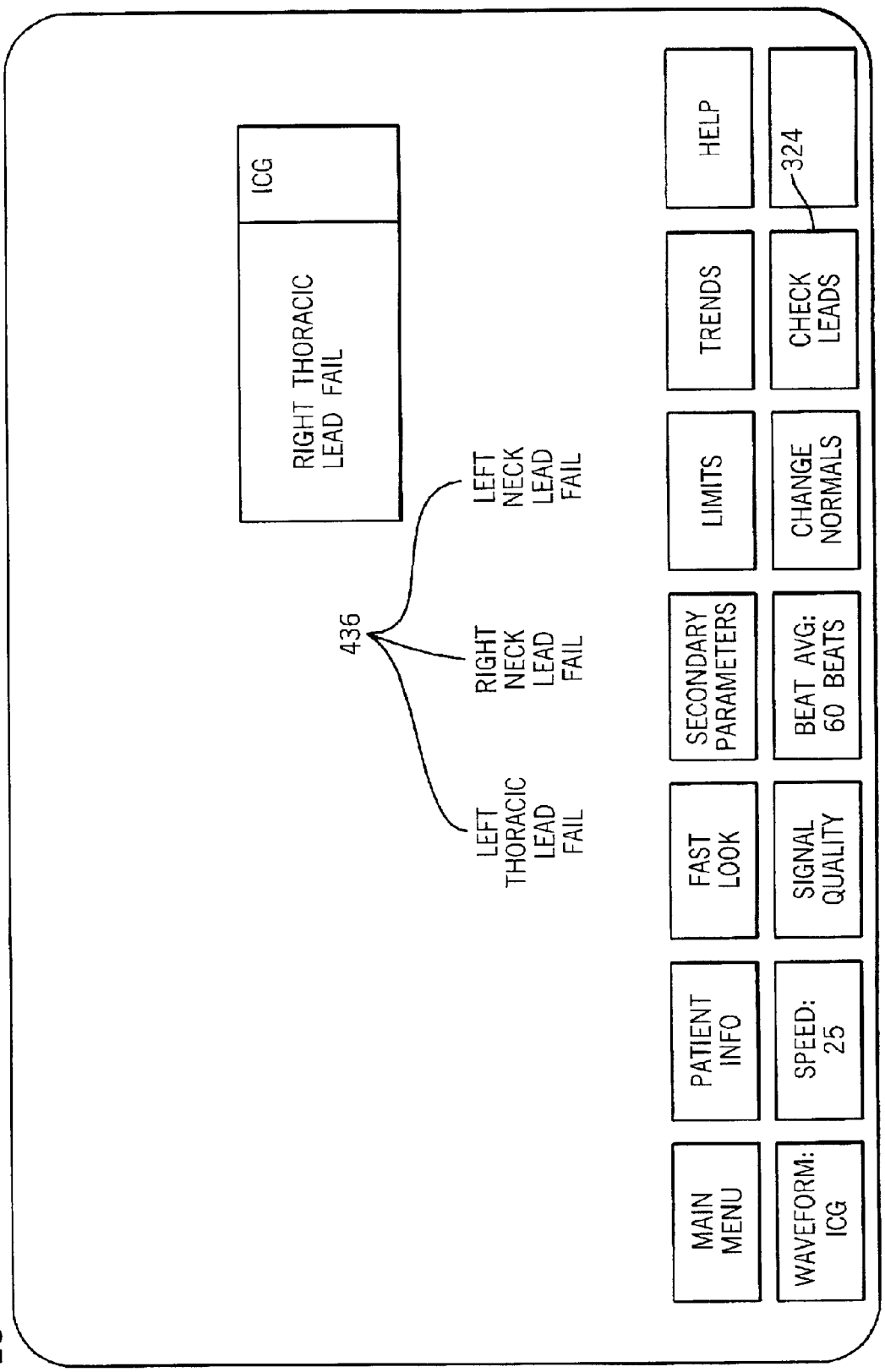
FIG. 19 is a check leads menu corresponding to FIG. 18 in which a failed lead condition is detected.

If the operator selects the check leads button 324, then a lead check of the electrodes 221a–221b, 222a–222b, 223a–223b, and 224a–224b is initiated as shown in FIG. 18. When monitoring cardiac flow parameters, electrodes are checked periodically for leads fail condition. During the lead check process, the cardiac flow waveform exhibits an approximately one-half second period of flat line 432 and the message "leads check" is displayed (434). The check leads menu option allows the system 100 to check for a leads fail condition in response to operator inputs. Should the monitor detect a leads fail condition, a message indicating the position of the failed lead may be displayed, as shown by messages 436 in FIG. 19.

Figure 20A:
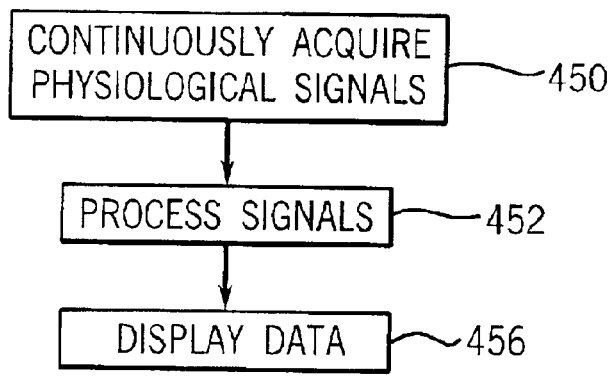
FIGS. 20A–20B are flowcharts showing the preferred operation of the patient monitoring system of FIG. 1.

Referring now to FIG. 20A, in operation and after system initialization, the monitoring system 100 continuously acquires the physiological signals from the patient using the input devices 105 (the electrodes $E_1$, $E_2$. . . $E_n$ and the sensors 141–146 and 155) at step 450. At step 452, the analysis module processes the physiological signals from the patient. At step 456, the processed data is displayed to the operator.

Figure 20B:
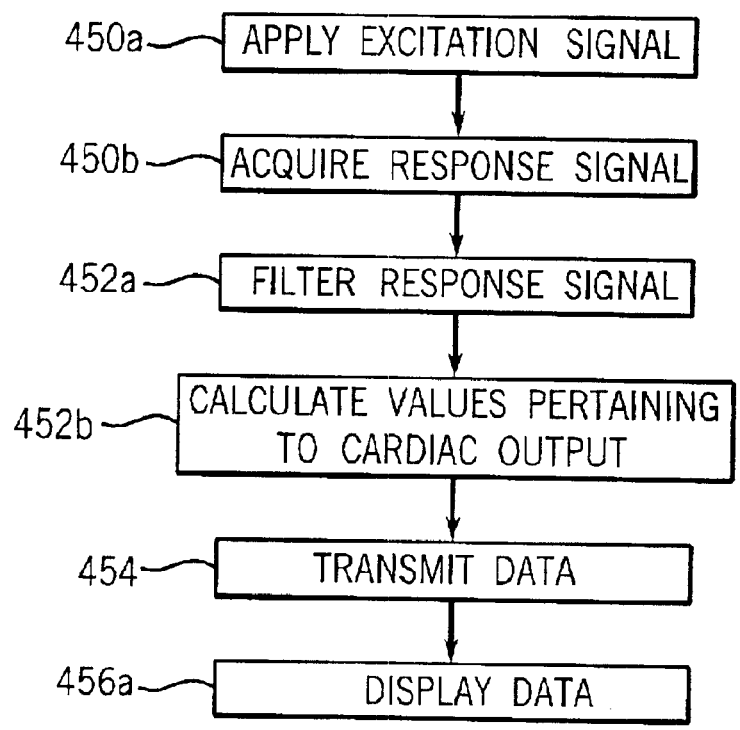

FIG. 20B shows this process in the context of the cardiac output data in one preferred manner of operation. Thus, in step 450a (corresponding to step 450), the monitoring system applies an excitation signal to a patient using electrodes 221a–221b and 222a–222b. The excitation signal is a low amplitude (e.g., 1–4 milliamps), high frequency (e.g., 30–100 kHz), constant magnitude alternating current which is applied to the thoracic volume. At step 450b (also corresponding to step 450), a response signal is acquired using the electrodes 223a–223b and the electrodes 224a–224b. The response signal is indicative of blood flow and is produced in response to the excitation signal. In particular, the voltage of the response signal is proportional to the impedance between the electrodes 223a–223b and the electrodes 224a–224b, and the impedance in turn is a function of an amount of blood located in a blood flow path that passes through the heart of the patient. The response signal indicates the response characteristics of the heart to the excitation signal and is usable to measure the impedance of the heart.

At steps 452a and 452b (corresponding to step 452), the analysis module 175 processes the response signal to produce a value pertaining to cardiac output. In the preferred embodiment, at step 452a, the response signal is electronically filtered to remove the change in impedance caused by respiration. At step 452b, the equations set forth in Tables 1 and 2 are then performed by the analysis module 175 to yield the sixteen preferred values pertaining to cardiac output set forth in Tables 1 and 2.

Step 454 is an additional step which is shown in FIG. 20B. At step 454, the cardiac output information is transmitted from the patient monitoring system 100 to a remote patient monitor by way of a local area network 210 of a medical facility in which the portable patient monitoring system 100 is located. This allows, at step 456a (corresponding to step 456), the cardiac output information to be displayed on a display at the remote patient monitor 205, 206. Therefore, a physician or nurse can monitor patient status while also attending to other tasks outside the patient's room. Of course, the cardiac output information can also be displayed at the display 202 which is directly coupled to the analysis module.

The patient monitoring system 100 also processes information from other sensors. For example, in connection with ECG monitoring, 12SL monitoring is performed. In the illustrated embodiment, ten electrodes are used to continuously acquire ECG signals from the patient (RA, LA, LL, RL, V1, V2, V3, V4, V5 and V6). The ECG signals are transmitted to the input terminal 130 of the console 110 via the interface cable 125. The ECG signals 111 are provided to the instrumentation amplifier 180 which combines, amplifies and filters the ECG signals resulting in a standard twelve-lead ECG. The resulting multi-lead ECG is provided to the A/D conversion circuit 170 which samples each lead of the multi-lead ECG to create a digital signal representing the multi-lead ECG, and provides the digital multi-lead ECG to the analysis module 175. The multi-lead ECG provided to the analysis module 175 includes ECG leads I, II, V1, V2, V3, V4, V5 and V6 which are acquired directly from the patient leads and leads III, aVR, aVF, and aVL which are derived.

The analysis module 175 includes an arrhythmia analyzer module which includes high and low frequency detect modules which evaluate each of the leads for high frequency and low frequency noise, a QRS detection module which detects signals falling within the physiologic band and which it recognizes as valid ECG signals, a QRS correlation module which passes the ECG data stream through a list of active templates, which are incrementally updated so that they are progressively changed along with the beat shape. The analysis module 175 further includes an arbitrator module which processes beats recognized by the QRS correlator and beats which do not match any of the existing templates, and a determination is made whether to create a new template and replace the least useful of the active templates. These would-be templates which are matched with the least frequency or have not been recently matched or classified as likely to be artifacts. The analysis module further includes a classifier module which receives the template information associated with the beats and takes all the feature and temporal measurements and arrives at a determination as to what is represented by that particular beat, that is a normal QRS, an atrial artificially paced normal QRS, a premature supraventricular QRS, ventricular artificially paced QRS, a ventricular premature QRS, a T wave, a P wave, a ventricular artificial pacing spike, an atrial artificial pacing spike or an artifact. The measurements made to determine individual beat characteristics are R amplitude, S amplitude, QRS polarity, T wave polarity, ST segment, noise level, PR interval, P wave presence, QT interval, QRS duration, RR interval, RR interval variance, pacemaker signals and rotation of cardiac vector. The analysis module further includes an arrhythmia call logic module which employs well-known criteria to make an arrhythmia call. These include the duration of usable ECG data, heart rate, the time between QRS complexes, the occurrence of a ventricular complex within a repolarization period, the occurrence of one or more ventricular beats preceded or followed by nonventricular beats, ST deviations of a predetermined magnitude, R-to-R intervals and the intervals between the QRS complex and a pacemaker spike. With this information, the arrhythmia call logic can determine if one of the following has occurred: an artifact, ventricular asystole, ventricular fibrillation, ventricular tachycardia, VT3–5, R-on-T, ventricular bradycardia, couplet, bigeminy, accelerated ventricular rhythm, pause, trigeminy, isolated premature ventricular complexes, ST deviation, tachycardia, bradycardia, irregular heartbeat or electronic pacemaker nonsensing. If an arrhythmia call is indicated, an appropriate alarm signal is provided to the display 202.

In operation, the analysis module 175 receives the ECG leads I, II, III, V1–V6, aVF, aVR, and aVL. Initially, the beat select section makes a template for each lead. From this point on, the QRS selector looks for the same shape. If it finds a match, the program classifies it as another QRS detection. In addition, the program slides the wave forms past one another looking for the optimal match. If the output of the filters in the acquisition modules exceed a preselected value, but there is no match, it is assumed that a different beat type has been detected and an additional set of templates are made for further matching tests. Thus, the beat selector uses a filter and template matching techniques to both detect and group by shape the QRS complexes which occur in the ECG record. The QRS detector also defines the points on the ECG record that can be used to align and time with maximum correlation, the respective beats of a beat type.

The program then determines which beat type will be used for the morphology measurements. The program uses the RR intervals and the location of any pacer spikes in order to decide which beat has the highest level of origin in the conduction system. Identical QRS shapes can even be subdivided as in the case of a sinus rhythm with premature beats. The selection is not dependent upon the number of beats per beat type but rather the beat type which is the most informative for analysis is the one sought after and any beat type with three or more complexes can qualify. The beat type that the computer considers to be most informative of normal conduction is often referred to as the primary beat.

After a primary beat has been chosen, each of its associated beats is used in generating a representative complex for each lead. This is done using the sample times generated by the QRS detector. These times not only indicate the occurrence of a QRS but also indicate when the QRS for a specific beat type are optimally matched. The representative complex is then generated with the median voltages from the aligned group of beats, that is, it is formed by taking, at each sample time, the middle voltage of the superimposed beats.

After the median for the primary cycle has been established for each of the twelve leads, the waves of each complex are identified. This is done separately for each lead. The program finds the points at which the signal crosses the baseline within each complex. If the crossing points define a wave that has an area greater than a predetermined value, the wave is considered to be significant. If the area is less than this value, the program considers the wave to be insignificant and it will not label it as a separate wave. The measurement matrix contains the amplitudes, with respect to QRS onset, and durations of all of the individuals waves, including the amplitude and duration of the P, P', Q, R and S waves, the amplitude of the T wave, the PR and QT intervals, the QRS duration and the STJ, STM and STE amplitudes.

The program then utilizes these measurements in making an interpretation. This includes a rhythm analysis and a morphology interpretation. The rhythm analysis first determines the origins of the predominant rhythm in the sample and chooses from the major categories consisting of electronic atrial pacing, atrial flutter, ectopic atrial rhythm, sinus rhythm, junction rhythm and atrial fibrillation.

The morphology interpretation will determine the existence of Wolff-Parkinson-White, atrial hypertrophy, QRS abnormalities such as low voltage QRS, pulmonary disease pattern, QRS axis, conduction abnormalities, ventricular hypertrophy, infarction, ST+T abnormality with ventricular hypertrophy, dating infarcts, epicardial injury, pericarditis, early repolarization, nonspecific ST elevation, subendocardial injury, nonspecific ST depression, digitalis effect, junctional ST depression, ischemia, QRS-T angle and QT interval.

Other monitoring applications are performed similarly to cardiac output monitoring. Thus, blood pressure information from the blood pressure sensor 141, pulse oximetry information from the pulse oximetry sensor 142, temperature information from the temperature sensor 143, carbon dioxide information from the carbon dioxide sensor 144, and respiration gas information from the respiration sensor 145 are acquired, processed, and displayed either locally at the display 202 or remotely at another display. All of the data may also be printed by the printer 201, stored in the data storage memory 195 for analysis or later recall, provided to the external storage device 203 for storage, and/or provided to remote devices 205 and 206 connected to the patient monitoring system by way of the hospital communication network.

Figure 21:
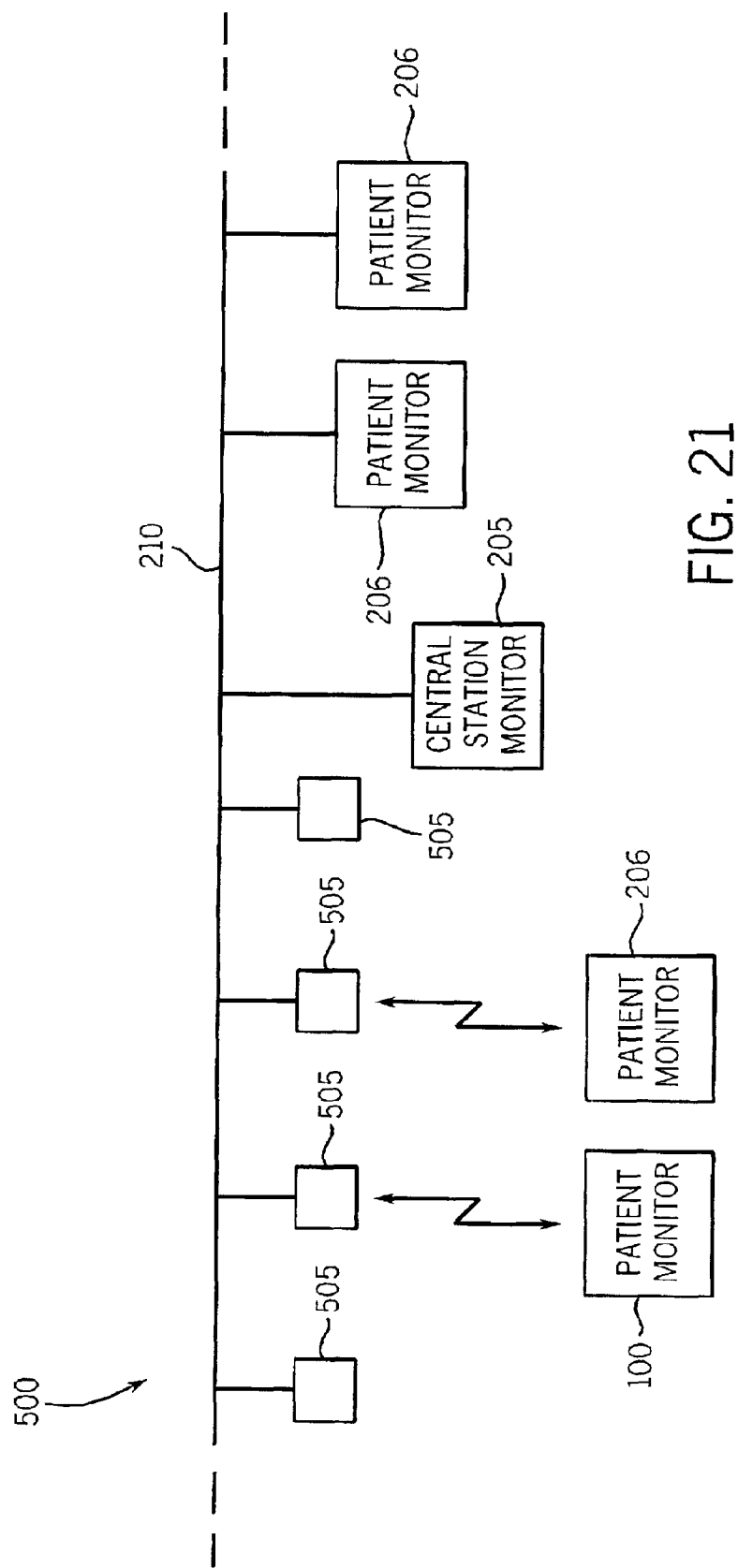
FIG. 21 is a block diagram showing the patient monitoring system of FIG. 1 networked with other monitoring devices.

Referring to FIG. 21, a patient monitoring network 500 is shown, some of the components of which have been previously described. The patient monitoring network 500 comprises the hospital communication network 210, a plurality of the patient monitoring systems 206 (preferably constructed in the same manner as the patient monitoring system 100 as previously described), and the central monitor 205. The hospital communication network establishes bed-to-bed communication and allows patient data to be sent to the central monitor 205. Patient data including cardiac output data can be communicated over the hospital communication network 210 and the patient monitors 205, 206 can view and trend data acquired from other patient monitors. Alarms may also be transmitted over the network 210.

To facilitate remote viewing, one of the menu selections that is preferably reachable by way of the more menus button 275 in FIG. 3 is a view other patients option. The view other patients option allows the operator to select any patient monitoring system 206 on the hospital communication network 210 to view at a particular monitoring system 100. Locally, the display screen is then divided in half and data from one patient is displayed on one half the screen and data from the other patient is displayed on the other half of the screen. Continuous waveform and parameter value data, such as cardiac output waveforms and parameters, is displayed for both patients.

As previously noted, the console 110 is preferably portable. The console 110 may for example comprise a carrying handle and weigh less than twenty pounds, or preferably less than 15 pounds, and most preferably about 12 pounds. Each patient monitoring system 100, 206 preferably includes a docking station capable of receiving the patient monitor console 110 and connecting the console to electrical power and to the hospital communication network 210. Additionally, the communication interface 197 is capable of establishing a wireless communication link between the patient monitoring system 100 and the hospital communication network 210.

To facilitate portability, the hospital communication network 210 includes a plurality of access points 505 and allows an operator to roam from one access point 505 to another while maintaining a connection to the network. The access points 505 connect the patient monitoring systems 100, 206 to the hospital communication network 210, and act as a bridge between the wired and wireless portions of the network 210. The areas covered by each access point 505 are overlapping to ensure continuous coverage. The monitoring system 100 switches automatically between hard-wired (docking station or cable connection) and wireless network communication.

The preferred embodiment of the patient monitoring system offers several advantages. First, the console 110 is portable. This allows for allows monitoring while the patient is in transport from the emergency room to the next stop for the patient. Additionally, the console 110 monitors not only cardiac output, but also 12 lead ECG and other parameters. Therefore, medical personnel only need one device to do all of their monitoring instead of a patient monitor along with a separate cardiac output monitor. Also, 12 lead analysis and other ECG analysis can be performed from a single monitor. This is important because space at a bedside is critical, and it is less expensive for the hospital to purchase only one unit. Further, cardiac output data can be trended along with all other paramater data. This allows the clinicians to compare the changes in cardiac output parameters alongside all other monitored parameters over time. This is important because correct diagnoses often need to take into account all parameter data, instead of only looking at one parameter. Usually a change in one parameter will also indicate a change in other parameters, and medical personnel wish to take into account all of these changes when evaluating the treatment of a patient.

What is claimed is:

1. A patient monitoring system comprising:
   (A) a non-invasive cardiac output sensor, the non-invasive cardiac output sensor being capable of acquiring a signal from a patient indicative of blood flow through a heart of the patient;
   (B) a multi-lead electrocardiogram (ECG) sensor, the multi-lead ECG sensor comprising a plurality of ECG electrodes capable of acquiring a plurality of ECG signals from the patient; and
   (C) a patient monitor console, including
      (1) an analysis module, the analysis module being coupled to the non-invasive cardiac output sensor and to the multi-lead ECG sensor, the analysis module processing the signal from the patient indicative of blood flow to produce a value pertaining to cardiac output, and
      (2) a display, the display being coupled to the analysis module, and the display configured to display the value pertaining to cardiac output and a plurality of ECG waveform generated based on the ECG signals;
   a communication interface capable of establishing a communication link between the patient monitoring system and a local area network of a medical facility in which the patient monitoring system is located;
   a plurality of additional sensors; and
   a dial operator input device,
   wherein the display displays a cardiac output parameter window that allows access to non-invasive cardiac output options and a plurality of additional parameter windows corresponding to parameters sensed by respective ones of the plurality of additional sensors, wherein the dial operator input device is rotatable in either direction to highlight different parameter windows, and wherein, when the cardiac output parameter window is highlighted, and the dial operator input device is pressed while the cardiac output parameter window is highlighted, the display displays a plurality of cardiac output menu options, the cardiac output menu options being selectable by an operator to cause the display to display additional information pertaining to cardiac output to the operator and to receive inputs from the operator to adjust processing of the signal from the cardiac output sensor.

2. A system according to claim 1, wherein the non-invasive cardiac output sensor further comprises first and second electrodes, and wherein the analysis module produces the value pertaining to cardiac output by determining an impedance between the first and second electrodes, the impedance between the first and second electrodes being a function of an amount of blood located in a blood flow path that passes through the heart of the patient.

3. A system according to claim 2, wherein the plurality of menu options includes an option that causes the patient monitoring system to test placement of the first and second electrodes on the patient.

4. A system according to claim 2, wherein the plurality of menu options includes a help option that causes the display to display help information describing proper electrode placement locations on the patient.

5. A system according to claim 2, wherein the plurality of menu options includes a help option that causes the display to display help information describing proper skin preparation prior to electrode placement on the patient.

6. A system according to claim 2, wherein the plurality of menu options includes an option to change a type of impedance waveform that is displayed to an operator.

7. A patient monitoring system comprising:
(A) a non-invasive cardiac output sensor, the non-invasive cardiac output sensor being capable of acquiring a signal from a patient indicative of blood flow through a heart of the patient:
(B) a communication interface, the communication interface being capable of establishing a communication link between the patient monitoring system and a local area network of a medical facility in which the patient monitoring system is located; and
(C) a patient monitor console, including
  (1) an analysis module, the analysis module being coupled to the non-invasive cardiac output sensor, the analysis module processing the signal from the patient indicative of blood flow to produce a value pertaining to cardiac output, and
  (2) a display, the display being coupled to the analysis module,
and the display displays the value pertaining to cardiac output,
a plurality of additional sensors; and
and a dial operator input device,
wherein the communication interface is capable of transmitting the value pertaining to cardiac output over the local area network;
wherein the display displays a cardiac output parameter window that allows access to non-invasive cardiac output options and a plurality of additional parameter windows corresponding to parameters sensed by respective ones of the plurality of additional sensors,
wherein the dial operator input device is rotatable in either direction to highlight different parameter windows, and wherein, when the cardiac output parameter window is highlighted, and the dial operator input device is pressed while the cardiac output parameter window is highlighted, the display displays a plurality of cardiac output menu options, the cardiac output menu options being selectable by an operator to cause the display to display additional information pertaining to cardiac output to the operator or to receive inputs from the operator to adjust processing of the signal from the cardiac output sensor.

8. A system according to claim 7, wherein the non-invasive cardiac output sensor further comprises first and second electrodes, and wherein the analysis module produces the value pertaining to cardiac output by determining an impedance between the first and second electrodes, the impedance between the first and second electrodes being a function of an amount of blood located in a blood flow path that passes through the heart of the patient; and wherein the plurality of menu options includes an option that causes the patient monitoring system to test placement of the first and second electrodes on the patient.

9. A system according to claim 7, wherein the non-invasive cardiac output sensor further comprises first and second electrodes, and wherein the analysis module produces the value pertaining to cardiac output by determining an impedance between the first and second electrodes, the impedance between the first and second electrodes being a function of an amount of blood located in a blood flow path that passes through the heart of the patient; and wherein the plurality of menu options includes a help option that causes the display to display help information describing proper electrode placement on the patient.

10. A system according to claim 7, further comprising a multi-lead electrocardiogram (ECG) sensor comprising a plurality of ECG electrodes capable of acquiring a plurality of ECG signals from the patient, and wherein the display displays an ECG waveform generated based on the ECG signals.

11. A system according to claim 10, wherein the plurality of ECG signals include leads I, II, III, V1, V2, V3, V4, V5, V6, aVR, aVL and aVF.

12. A patient monitoring method comprising:
(A) a non-invasive cardiac output sensor capable of acquiring a signal from a patient indicative of blood flow through a heart of the patient, the non-invasive cardiac output sensor comprising first and second electrodes;
(B) a multi-lead electrocardiogram (ECG) sensor comprising a plurality of ECG electrodes capable of acquiring a plurality of ECG signals from the patient;
(C) a blood pressure sensor capable of acquiring blood pressure information from the patient;
(D) a pulse oximetry sensor capable of acquiring pulse oximetry information from the patient;
(E) a carbon dioxide sensor capable of acquiring information pertaining to carbon dioxide content in respiratory gas of the patient;
(F) a patient monitor console, including
  (1) an analysis module coupled to the non-invasive cardiac output sensor, the multi-lead ECG sensor, the blood pressure sensor, the pulse oximetry sensor, and the carbon dioxide sensor, the analysis module processing the signal from the patient indicative of blood flow to produce a value pertaining to cardiac output, the analysis module producing the value pertaining to cardiac output by determining an impedance between the first and second electrodes, the impedance between the first and second electrodes being a function of an amount of blood located in a blood flow path that passes through the heart of the patient, the value pertaining to cardiac output pertains to a volume of blood pumped by the heart per unit time, (2) a display coupled to the analysis module, and the display displaying the ECG waveform, the value pertaining to cardiac output, the blood pressure information, the carbon dioxide information, and the pulse oximetry information, (3) a communication interface capable of establishing a communication link between the patient monitoring system and a local area network of a medical facility in which the patient monitoring system is located, and (4) a dial operator input device, wherein, the display displays a plurality of parameter windows which respectively display the non-invasive cardiac output information, the ECG information, the blood pressure information, the pulse oximetry information, and the carbon dioxide information;

wherein the dial operator input device is rotatable in either direction to highlight different parameter windows; and wherein, when the non-invasive cardiac output parameter window is highlighted, and the dial operator input device is pressed while the non-invasive cardiac output parameter window is highlighted, the display displays a plurality of non-invasive cardiac output menu options, the non-invasive cardiac output menu options being selectable by an operator to cause the display to display additional information pertaining to non-invasive cardiac output to the operator or to receive inputs from the operator to adjust processing of the signal from the non-invasive cardiac output sensor.

13. A system according to claim 12, wherein the plurality of ECG signals include eight leads which are acquired directly and four leads which are derived.

14. A system according to claim 12, wherein the plurality of ECG signals include leads I, II, III, V1, V2, V3, V4, V5, V6, aVR, aVL and aVF.

15. A patient monitoring console comprising:

(A) an input for a non-invasive cardiac output sensor capable of acquiring a signal from a patient indicative of blood flow through a heart of the patient;

(B) an input for a multi-lead electrocardiogram (ECG) sensor comprising a plurality of ECG electrodes capable of acquiring a plurality of ECG signals from the patient;

(C) an analysis module coupled to the input for the non-invasive cardiac output sensor and to the input for the multi-lead ECG sensor, the analysis module configured to process the signal from the patient indicative of blood flow to produce a value pertaining to cardiac output and configured to control a display to simultaneously display a plurality of ECG waveforms and a non-invasive cardiac output waveform;

a communication interface capable of wirelessly connecting the patient monitoring console to a local area network of a medical facility in which the patient monitoring console is located;

a communication interface capable of connecting the patient monitoring console to the local area network of the medical facility in which the patient monitoring console is located by a wired connection, wherein the patient monitoring console is configured to be automatically switched between wireless connection to the network and wired connection to the network.

a plurality of additional sensors; and a dial operator input device, wherein the display displays a non-invasive cardiac output parameter window and a plurality of additional parameter windows corresponding to parameters sensed by respective ones of the plurality of additional sensors;

wherein the dial operator input device is rotatable in either direction to highlight different parameter windows, and wherein, when the non-invasive cardiac output parameter window is highlighted, and the dial operator input device is pressed while the non-invasive cardiac output parameter window is highlighted, the display displays a plurality of non-invasive cardiac output menu options, the non-invasive cardiac output menu options being selectable by an operator to cause the display to display additional information pertaining to noninvasive cardiac output to the operator and to receive inputs from the operator to adjust processing of the signal from the non-invasive cardiac output sensor.

16. The console of claim 15, wherein the non-invasive cardiac output sensor further comprises first and second electrodes, and the plurality of menu options includes an option that causes the patient monitoring system to test placement of the first and second electrodes on the patient.

17. The console of claim 15, wherein the non-invasive cardiac output sensor further comprises first and second electrodes, and the plurality of cardiac output menu options includes a help option that causes the display to display help information describing proper electrode placement locations on the patient.

18. The console of claim 15, wherein the non-invasive cardiac output sensor further comprises first and second electrodes, and the plurality of non-invasive cardiac output menu options includes a help option that causes the display to display help information describing proper skin preparation prior to electrode placement on the patient.

19. The console of claim 15, wherein the plurality of non-invasive cardiac output menu options includes an option to change a type of non-invasive cardiac output waveform that is displayed to an operator.

* * * * *